United States Patent [19]
White

[11] Patent Number: 5,237,520
[45] Date of Patent: Aug. 17, 1993

[54] FOOT MEASUREMENT AND FOOTWEAR SIZING SYSTEM

[75] Inventor: Jay P. White, Bend, Oreg.

[73] Assignee: Foot Image Technology, Inc., Bend, Oreg.

[21] Appl. No.: 891,166

[22] Filed: May 29, 1992

Related U.S. Application Data

[63] Continuation of Ser. No. 520,592, May 11, 1990, Pat. No. 5,128,880.

[51] Int. Cl.⁵ .................. G06F 15/00; A61B 5/103
[52] U.S. Cl. ..................... 364/560; 33/512; 128/779; 356/376; 364/550; 12/142 N
[58] Field of Search ............. 364/550, 413.13, 413.14, 364/413.22, 522, 558, 560, 561, 512; 33/512, 515; 356/2, 12, 376, 357; 358/3, 96; 128/779

[56] References Cited

U.S. PATENT DOCUMENTS

| | | | |
|---|---|---|---|
| 2,009,471 | 7/1935 | Brauer et al. | |
| 3,192,627 | 7/1965 | Levitt et al. | 33/515 |
| 3,391,392 | 7/1968 | Doyle | 340/172.5 |
| 3,457,647 | 7/1969 | Cohen et al. | 33/515 |
| 3,573,546 | 4/1971 | Hemery | 318/578 |
| 3,609,322 | 9/1971 | Burnett et al. | 318/578 |
| 3,614,237 | 10/1971 | Kyle et al. | |
| 3,696,456 | 10/1972 | Dunham et al. | 12/146 L |
| 3,764,877 | 10/1973 | Meyer | 318/578 |
| 3,814,521 | 6/1974 | Free | |
| 3,878,761 | 4/1975 | Makowski | 409/122 |
| 3,980,938 | 9/1976 | Nakagoshi et al. | 318/578 |
| 4,084,244 | 4/1978 | Floter | 364/474.03 |
| 4,117,385 | 9/1978 | Limbach et al. | 318/578 |
| 4,158,507 | 6/1979 | Himmel | 356/376 |
| 4,164,815 | 8/1979 | Salomon | 33/515 |
| 4,185,918 | 1/1980 | DiMatteo et al. | 356/375 |
| 4,215,960 | 8/1980 | Tsuzuki | 409/121 |
| 4,224,670 | 9/1980 | Yamazaki | 364/474.03 |
| 4,267,728 | 5/1981 | Manley et al. | 128/779 |
| 4,296,473 | 10/1981 | Imazeki et al. | 364/520 |
| 4,299,491 | 11/1981 | Waters et al. | 356/376 |
| 4,328,050 | 5/1982 | Ashizawa et al. | 148/9 R |
| 4,385,360 | 5/1983 | Yamada et al. | 364/514 |
| 4,394,608 | 7/1983 | Tryber et al. | 318/578 |
| 4,406,544 | 9/1983 | Takada et al. | 356/476 |
| 4,412,364 | 11/1983 | Orea | 12/146 L |
| 4,424,570 | 1/1984 | Imazeki et al. | 364/520 |
| 4,433,275 | 2/1984 | Imazeki et al. | |
| 4,449,699 | 5/1984 | Ashizawa et al. | |
| 4,450,014 | 5/1984 | Hayasaki et al. | |
| 4,452,057 | 6/1984 | Davies et al. | |
| 4,454,618 | 6/1984 | Curchod | 12/146 L |
| 4,458,689 | 7/1984 | Sorenson et al. | |
| 4,472,782 | 9/1984 | Suzuki | |
| 4,517,504 | 5/1985 | Honji et al. | |
| 4,534,365 | 8/1985 | Bonetta et al. | |
| 4,538,353 | 9/1985 | Gardner | 33/515 |
| 4,541,054 | 9/1985 | Peck et al. | |
| 4,558,420 | 12/1985 | Gerber | |
| 4,575,805 | 3/1986 | Moermann et al. | |
| 4,598,376 | 7/1986 | Burton et al. | |
| 4,600,016 | 7/1986 | Boyd et al. | |
| 4,603,285 | 7/1986 | Matsuura et al. | |

(List continued on next page.)

FOREIGN PATENT DOCUMENTS 3812287 10/1989 Fed. Rep. of Germany .
2607252 5/1988 France .
WO90/05345 5/1990 PCT Int'l Appl. .

OTHER PUBLICATIONS

*Medical and Biological Engineering and Computing,* vol. 18, No. 5, Sep. 1980, Stevenage FB pp. 674–684; Betts et al.; Static and Dynamic Foot-Pressure Measurements in Clinical Orthopeadics.

(List continued on next page.)

Primary Examiner—Kevin J. Teska
Attorney, Agent, or Firm—Merchant, Gould, Smith, Edell, Welter & Schmidt

[57] ABSTRACT

Systems and methods are provided for measuring bottom facing surfaces of a foot which comprise placing the foot against a reference surface, projecting light against the foot, and displaying an image of the foot on a visual display to differentiate relative distances of portions of the foot from the reference surface. In addition, the image differentiates portions of the foot exerting different pressures against the reference surface.

6 Claims, 38 Drawing Sheets

U.S. PATENT DOCUMENTS

| | | |
|---|---|---|
| 4,604,807 | 8/1986 | Bock et al. . |
| 4,662,079 | 5/1987 | Graf et al. ............................ 33/512 |
| 4,665,492 | 5/1987 | Masters . |
| 4,745,290 | 5/1988 | Frankel et al. . |
| 4,803,348 | 2/1989 | Lohrey et al. . |
| 4,817,222 | 4/1989 | Shafir . |
| 4,858,621 | 8/1989 | Franks ............................ 33/512 X |
| 4,867,570 | 9/1989 | Sorimachi et al. . |
| 4,876,758 | 10/1989 | Rolloff et al. ..................... 12/142 N |
| 4,897,924 | 2/1990 | Tepley ............................. 33/512 X |
| 4,917,105 | 4/1990 | Tittola et al. ..................... 33/515 X |
| 4,952,149 | 8/1990 | Duret et al. . |
| 5,033,014 | 7/1991 | Carver et al. ............... 364/474.24 X |
| 5,088,503 | 2/1992 | Seitz ................................. 12/142 N |
| 5,123,169 | 6/1992 | White et al. ..................... 33/515 X |
| 5,126,948 | 6/1992 | Mitchell et al. ................ 364/474.03 |
| 5,128,870 | 7/1992 | Erdman et al. ............. 364/474.24 X |
| 5,128,880 | 7/1992 | White ............................... 364/561 X |

OTHER PUBLICATIONS

Patent Abstracts of Japan, vol. 12, No. 100 (P-683) (2947), dated Apr. 1988, Application No. 611-77920 concerns a shape measuring instrument for the feet.

Article from *Journal of Prosthetics and Orthotics*, vol. 1, No. 3, pp. 182-186 entitled "Computer Aided Design and Computer Aided Manufacturing of Foot Orthoses".

Harvard Business School publication 9-188-083 titled "The Florsheim Shoe Company-Express Shop", dated 1988, 14 pp.

Letter dated Apr. 4, 1990, from Dimensional Measurement Systems, Inc., from Mr. Tom Barnes, Product Director, Red Wing Shoe Company, Inc.

Article from *Applied Optics*, vol. 23, No. 21, pp. 3837-3844 entitled "Laser Range Finder Based on Synchronized Scanners", dated Nov. 1, 1984.

Article from *Handbook on Non-Topographic Photogrammetry*, pp. 167-184 entitled "Moiré Topography Systems and Potential Applications".

Article from *Photogrammetry*, pp. 579-562 entitled "Special Photogrammetric Systems and Applications".

Betts et al.; A device for measuring plantar pressures under the sole of the foot; Engineering in Medicine; vol. 7, p. 223 (1978).

William A. Rossi, "The 14-Point Fit Test" Jul. 1987, Footwear News Magazine.

Jackson Hogen, "The Best Boots for the Dollar", Aug. 1989, Snow Country Magazine, pp. 72-78.

"The All-Important Last," published in American shoemaking Magazine, Sep. 1988, pp. 49-52.

Brannock photograph.

Dana Fitter photograph.

Promotional Information photograph distributed by By Video, Inc.

Toshiba "Foot-Fitter" advertisement and promotional literature.

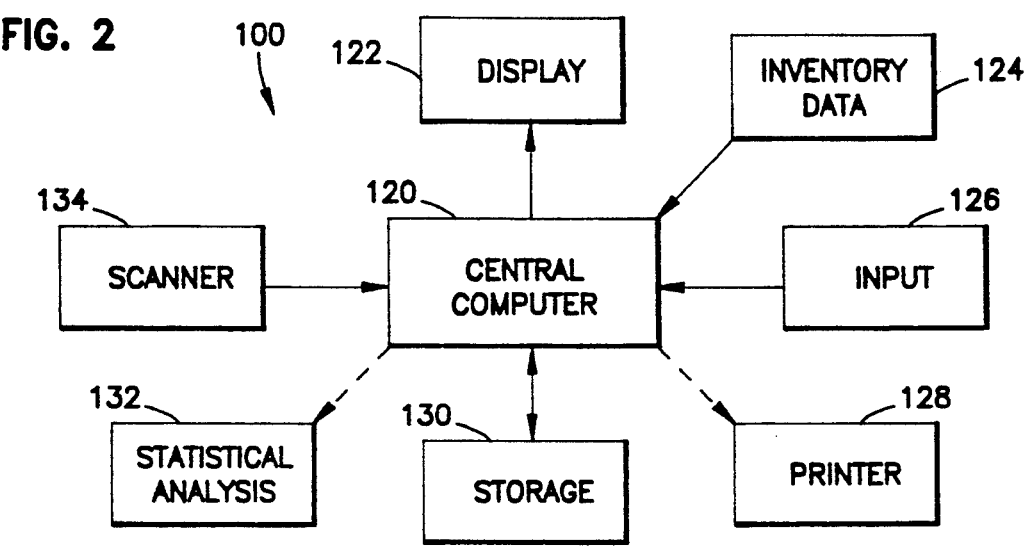
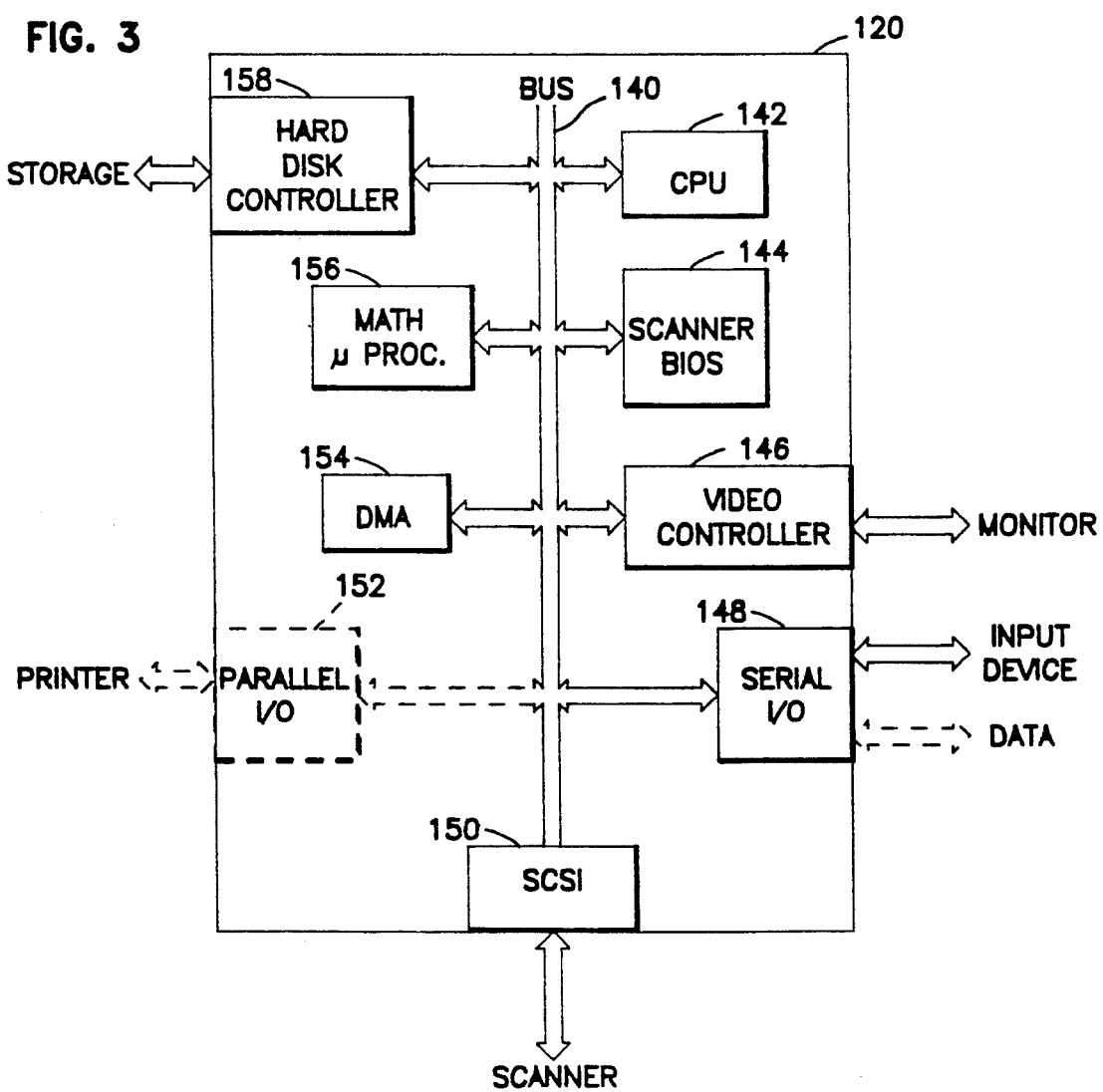

FIG. 12 ⟋214

EXISTING CUSTOMERS IN FILES

| CUSTOMER 1 .JAY WHITE | DATE 12-22-1989 SEX M |
| ARCH LENGTH R>10.5 L>12 VOLUME ZONE 6 | LAST # 3 FOOT TYPE 1 |
| CUSTOMER 2 .JAY WHITE | DATE 11-09-1989 SEX M |
| ARCH LENGTH R>11 L>13 VOLUME ZONE 5 | LAST # 4 FOOT TYPE 3 |
| CUSTOMER 3 .JAY TEST 11-25-89 | DATE 11-25-1989 SEX M |
| ARCH LENGTH R>10.5 L>12 VOLUME ZONE 6 | LAST # 4 FOOT TYPE 2 |
| CUSTOMER 4 .CHARLIE WEAVER | DATE 04-04-1990 SEX M |
| ARCH LENGTH R>11 L>11.5 VOLUME ZONE 5 | LAST # 4 FOOT TYPE 3 |
| CUSTOMER 5 .JAY WHITE 11-15 | DATE 11-15-1989 SEX M |
| ARCH LENGTH R>10.5 L>12 VOLUME ZONE 6 | LAST # 4 FOOT TYPE 2 |

TOTAL NUMBER OF PEOPLE IN STORAGE FILE 16

POINT TO THE CUSTOMER NUMBER YOU WANT TO SAVE UNDER
RETURN TO THE SELECTION MENU

FIG. 13 ⟋216

1. FULL NAME ................... JAY WHITE
2. ADDRESS STREET AND NUMBER ... 1620 SW OVERTURF
3. CITY - STATE - ZIP CODE ..... BEND OR 97702
4. PHONE NUMBER AND AREA CODE . 503 389-8844
5. AGE ......................... 35

CUSTOMER FILE NUMBER 17    FAST ACCESS NUMBER 1

1 2 3 4 5 6 7 8 9 0 -   BACKSPACE
Q W E R T Y U I O P     ENTER
A S D F G H J K L ;     RETURN
Z X C V B N M . .
SPACE BAR    SPACE BAR

FIG. 16

- Light weight – THIN
- Medium weight – NORMAL
- Heavy weight – THICK
- Multiple pairs – VERY THICK

INDICATE YOUR PREFERENCE IN SOCK THICKNESS

FIG. 17

- WORK BOOT AND SHOES
- SPORT BOOTS AND SHOES
- SAFETY WORK BOOT AND SHOES
- CASUAL BOOTS AND SHOES
- INSULATED WATERPROOF
- WESTERN BOOTS

INDICATE THE SHOE CATEGORY TO SELECT FROM

INDICATE YOUR OCCUPATION

- TRANSPORTATION
- CONSTRUCTION
- BUILDING TRADE
- AGRICULTURE
- HUNTING - OUTDOOR - SPORT
- HEAVY MANUFACTURING
- LIGHT MANUFACTURING
- HIGH TECH - ELECTRICAL
- SERVICE - UNIFORM
- LEISURE - CASUAL

INDICATE THE ENVIRONMENTAL CONDITION THE SHOE WOULD BE WORN MOST FREQUENTLY

- OIL
- TRACTION - WET
- CHEMICALS
- CONCRETE
- METAL CHIPS
- STATIC-ESD
- HEAT RESISTANT
- NON-MARKING
- ABRASION
- NONE OF THE ABOVE

TOUCH SCREEN TO DISPLAY 14 STYLE(S) SELECTED

| # | Style | Code | Size | | Size |
|---|---|---|---|---|---|
| 1 | DUNOON OXFORD | 9217 | 11.5 C | | 11.5 C |
| 2 | DUNOON OXFORD | 9207 | 11.5 C | | 11.5 C |
| 3 | RED WING SERVICE SHOE8184 | | 11.5 C | | 11.5 C |
| 4 | RED WING SERVICE SHOE8186 | | 11.5 C | | 11.5 C |
| 5 | RED WING SERVICE SHOE8181 | | 11.5 C | RED WING SERVICE SHOE8181 | 11.5 C |
| 6 | RED WING WORK SHOE | 9335 | 11.5 C | | 11.5 C |
| 7 | SERVICE OXFORD | 8595 | 11.5 C | | 11.5 C |

TOUCH SCREEN TO DISPLAY REMAINING MODELS

| # | Style | Code | Size | Style | Code | Size |
|---|---|---|---|---|---|---|
| 9 | IRISH SETTER PULL ON 8866 | | 11.5 C | IRISH SETTER PULL ON 8866 | | 11.5 C |
| 10 | IRISH SETTER BOOT H 8877 | | 11.5 C | IRISH SETTER BOOT H 8877 | | 11.5 C |
| 11 | IRISH SETTER BOOT | 8875 | 11.5 C | IRISH SETTER BOOT | 8875 | 11.5 C |
| 12 | RED WING WORK SHOE | 8952 | 12 C | RED WING WORK SHOE | 8952 | 12 C |
| 13 | PECOS PULL ON BOOT | 1184 | 11.5 C | PECOS PULL ON BOOT | 1184 | 11.5 C |
| 14 | IRISH SETTER PULL ON 8866 | | 11.5 C | IRISH SETTER PULL ON 8866 | | 11.5 C |

TOUCH SCREEN TO DISPLAY REMAINING MODELS
DO YOU WANT TO ADJUST FITTING SPECIFICATIONS (1-Yes / 2-No) ?

| 1 | 2 |

FIG.29

```
 9  IRISH SETTER PULL ON 8866   11.5  C                                11.5  C
10  IRISH SETTER BOOT    M 8877 11.5  C    IRISH SETTER BOOT  M 8877  11.5  C
11  IRISH SETTER BOOT      8875 11.5  C                                11.5  C
12  RED WING WORK SHOE     8952 12    C                                12    C
13  PECOS PULL ON BOOT     1184 11.5  C                                11.5  C
14  IRISH SETTER PULL ON 8866   11.5  C                                11.5  C

TOUCH SCREEN TO DISPLAY REMAINING MODELS
[1] 10 MENU  [2] COMPLETE HARDCOPY  [3] SHOES LISTED ONLY  [4] NO INVENTORY CHECK

```
          ENTER THE NUMBER OF THE CATEGORY YOU WANT TO ADJUST

[01] SEX                    >>>[02] FOREFOOT WIDTH
    [03] SOCK THICKNESS         >>>[04] HEEL WIDTH
    [05] FIT PRESSURE           >>>[06] FOOT TYPE
 >>>[07] TIE-UP CATEGORY           [08] CURVE LAST ZONE
 >>>[09] ENVIRONMENTAL EXPOSURE >>>[10] PRONATION
    [11] FOOT SIZE              >>>[12] VOLUME

POINT TO CATEGORY [##] -GO- TO CONTINUE >>>

THE >>> SIGN INDICATES THE CATEGORIES THAT MAY REQUIRE ADJUSTMENT TO ALLOW
                 MORE PRECISE FITTING OF YOUR FOOT

ENTER THE NUMBER OF THE CATEGORY YOU WANT TO ADJUST

[01] SEX                          [02] FOREFOOT WIDTH
[03] SOCK THICKNESS          >>>[04] HEEL WIDTH
[05] FIT PRESSURE            >>>[06] FOOT TYPE
>>>[07] FOOTWEAR CATEGORY    >>>[08] CURVE LAST ZONE
>>>[09] ENVIRONMENTAL EXPOSURE  >>>[10] PRONATION
[11] FOOT SIZE               >>>[12] VOLUME

YOUR HEEL WIDTH ZONE IS >> 4
CHANGE TO [1]Ex-Nar [2]Nar [3]Med [4]Wide [5]Ex-Wide >>

| 1 | 2 | 3 | 4 | 5 |

FIG. 32

ENTER THE NUMBER OF THE CATEGORY YOU WANT TO BRANCH TO

[1] SELECT SHOE FOR NEXT PERSON   [2] MAKE DATA CHANGES
[3] FIT-SCAN CONTROL PROGRAM      [4] RED WING PRODUCT CATALOG
[5] LAST OVERLAY VIEWING          [6] FIT AID RECOMMENDATIONS

CATEGORY SELECTION [#] >>

| 1 | 2 | 3 | 4 | 5 | 6 |

FIG. 35

```
RED WING SHOE INFORMATION COPYRIGHT

COMFORT SLIPON ESD SHOE
          STYLE 8606        LAST NUMBER 192
          S E X M           CURVE LAST ZONE 3-4
              FOOT  TYPE   SUITABILITY
       G-GOOD M-MODIFY TYPE 1 M TYPE 2 G TYPE 3 G
                  SIZES AVAILABLE
          AAA:                D: 6-16
          AA:                 E:
          A:                  EE: 7-13
          B: 10-14            EEE:
          C:                  H:
                    F E A T U R E S
LINER CAMBRELLE              INSULATION
INSOLE CUSHION LEATHER COVERED ESD   DRESSING  POLISH
S H A N K
O U T E R  BLACK COWHIDE
   COUNTER WATERPROOFED SHAPED REINFORCER
CONSTRUCTION CEMENT WEDGE
OUTER  SOLE  SOFTIE URETHANE ESD WEDGE NON SLIP SOLE AND HEEL
SPECIAL FEATURES  LEATHER PADDED COLLAR
[PAGE 1] [PAGE 2] [PAGE 3] [PAGE 4] [PAGE 5] [FIT THIS STYLE]
```

```
              QUICK FIT  DATE 04-05-1990

TOE LENGTH R>10  L>11    WIDTH ZONE R> 2  L> 1
     ARCH LENGTH R>10.5 L>12  HEEL ZONE 4  CURVE ZONE 2  FOOT TYPE 3

1  FEMALE  2 MALE  3 RETURN TO SELECTION MENU

| | | |
|---|---|---|
| 861 SAFETY CASUAL 6622 | 871 SAFETY OXFORD 2225 | 881 SAFETY BOOT 8" 2248 |
| 862 SAFETY ATHLETIC 6650 | 872 SAFETY OXFORD 2226 | 882 SAFETY BOOT 8" 2204 |
| 863 SAFETY SLIP ON 8703 | 873 SAFETY COMFORT 6604 | 883 SAFETY BOOT MET 4106 |
| 864 SAFETY MOCCASIN 6633 | 874 SAFETY BOOT 6" 2245 | 884 SAFETY BOOT MET 4128 |
| 865 SAFETY OXFORD 8701 | 875 SAFETY BOOT 6667 | 885 SAFETY BOOT MET 4108 |
| 866 SAFETY ATHLETIC 6655 | 876 SAFETY BOOT 6" 2243 | 886 SAFETY BOOT COLD 4401 |
| 867 SAFETY ATHLETIC 6656 | 877 SAFETY BOOT 6" 2224 | 887 SAFETY BOOT INS. 4114 |
| 868 SAFETY ATHLETIC 6652 | 878 SAFETY CHUKKA 6670 | 888 SAFETY BOOT HAZ 4429 |
| 869 SAFETY ATHLETIC 6653 | 879 SAFETY BOOT 8" 2233 | 889 SAFETY BOOT HAZ 4430 |
| 870 SAFETY COMFORT 6662 | 880 SAFETY BOOT 8" 2208 | 890 SAFETY BOOT INS. 4412 |

PAGE 3

[TO PAGE 1] [TO PAGE 2] [TO PAGE 3] [TO PAGE 4] [TO PAGE 5]    [TO MAIN SCREEN]

IRISH SETTER SPORT BOOT
STYLE 877   LAST NUMBER 23
S E X M   CURVE LAST ZONE 3-4
FOOT TYPE SUITABILITY
G-GOOD M-MODIFY TYPE 1 G TYPE 2 G TYPE 3 G
SIZES AVAILABLE

TOUCH VIEW TO ZOOM 263
263'
263"

| | |
|---|---|
| AAA: | D: 5-16 |
| AA: | E: 7-13 |
| A: 9-14 | EE: 7-13 |
| B: 8-18 | EEE: |
| C: 7.5-13 | H: 8-11 |

F E A T U R E S
LINING   LEATHER LINED VAMP
INSOLE   SWEAT RESISTANT OAK LEATHER
INSULATION  SWEAT RESISTANT OAK LEATHER
FINISH   RED WING OIL

S H A N K
L E A T H E R 8" FULL GRAIN OIL TANNED WATER REPELL ORO RUSSET
C O U N T E R
CONSTRUCTION GOODYEAR LEATHER WELT SEWN HEEL SEAT/WHITE RUBBER MIDSOLE
OUTER S O L E CUSHION CREPE WEDGE W/TRACTION TRED
SPECIAL FEATURES BOLLED TOP BAND/WRAP MOC/MISMATED TO ORDER

PAGE 1   PAGE 2   PAGE 3   PAGE 4   PAGE 5      MAIN SCREEN

FIG. 53

RECOMMENDED CUSTOM SHOE MODIFICATIONS FOR JAY WHITE

••• INDICATES FIT AID
>>> INDICATES SHOE MODIFICATION                             PURCHASE PRICE

PRONATION CONTROL
••• Eagle Insole                                                13.20
••• Impact Insole                                                7.20
                    DIMENSIONAL MODIFICATIONS
••• volume reduction shim                                        5.00
••• metatarsal pads                                              0.00
>>> lace pattern adjustment                                      0.00
>>> forefoot medial stretch                                      0.00
                    SOCK RECOMMENDATIONS
••• Cotton Tube Sock                                             4.00
••• Cotton Fitted Sock                                           4.00
••• All Around Sock                                              6.50
••• Wool Tube Sock                                               5.50
••• Eagle Polywick Sock                                          9.00
••• Duo-Therm Sock                                               7.25
••• Wick Duncan Orlon                                            5.00
STRIKE ANY KEY TO DISPLAY REMAINING PRODUCTS

FIG. 54

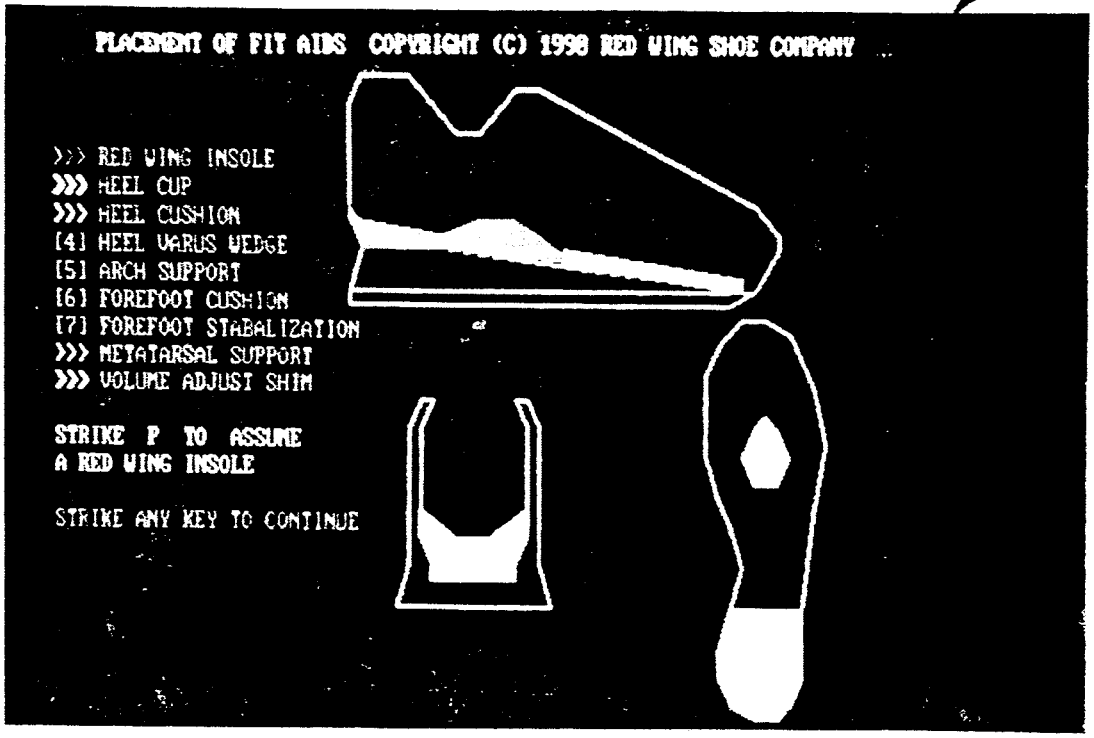

PLACEMENT OF FIT AIDS  COPYRIGHT (C) 1990 RED WING SHOE COMPANY

>>> RED WING INSOLE
>>> HEEL CUP
>>> HEEL CUSHION
[4] HEEL VARUS WEDGE
[5] ARCH SUPPORT
[6] FOREFOOT CUSHION
[7] FOREFOOT STABALIZATION
>>> METATARSAL SUPPORT
>>> VOLUME ADJUST SHIM

STRIKE P TO ASSUME
A RED WING INSOLE

STRIKE ANY KEY TO CONTINUE

FIG. 57

```
COPYRIGHT (C) 1989   RED WING SHOE COMPANY

SEARCH ITEMS BY:

[1] STORAGE NUMBER OF CUSTOMER
        [2] ALPHABETICAL SEARCH
        [3] DATE CUSTOMER ENTERED
        [4] STEP AND INCREMENT
        [5] LABEL CREATION AND PRINT CONTROL
        [6] RETURN TO RED WING SCAN CONTROL

ENTER THE SEARCH METHOD WANTED
```

FIG. 58

```
TYPE THE LAST NAME OF THE PERSON YOU WISH TO LOCATE

MAXIMUM OF 30 CHARACTERS >>? JAY WHITE_
```

FOOT MEASUREMENT AND FOOTWEAR SIZING SYSTEM

This is a continuation of application Ser. No. 07/520,592, filed May 11, 1990, now issued as U.S. Pat. No. 5,128,880 on Jul. 7, 1992.

FIELD OF THE INVENTION

This invention relates in general to the footwear manufacturing process including sales from a retail store, footwear design, last production, and finally the manufacturing of footwear. More particularly, it relates to an integrated computerized system for measuring and sizing feet and providing custom fit footwear for customers while maintaining optimized inventory of footwear for retail stores and manufacture of footwear. In addition, through statistical analysis of customer orders, it can be determined which footwear lasts are most likely to be required for producing footwear to fit a particular portion of the general population. This system thereby enables more accurate and efficient production of footwear and lasts for the general public consumption. Further, the present invention utilizes the foot sizing method and last production method disclosed in a co-pending U.S. patent application Ser. No. 416,624, filed Oct. 3, 1989, now issued as U.S. Pat. No. 5,123,169 on Jun. 23, 1992, hereinafter referred to as the TWAC ™ measurement system.

BACKGROUND OF THE INVENTION

Throughout modern history, the footwear industry has been a highly specialized and competitive environment. Most footwear manufacturers have felt a need to be as efficient as possible while providing high quality footwear for the majority of consumers. In recent years, this desire for efficiency has been increased due to the rise in international trade and competition as well as increased consumer demand. Therefore, footwear manufacturers have found it necessary to adapt to the market conditions by providing as many styles and sizes of shoes as possible to the public to better serve the needs of the consumers. Until recently, computerized automation of the footwear industry has been relatively limited; however, with the advent of more sophisticated computing machines and software to drive the computing machines, it has become possible to integrate the entire process of manufacturing footwear. The present invention provides a solution to this need for improved productivity and efficiency by integrating the entire process of selling retail footwear. As will be discussed below, the present invention seeks to integrate the entire footwear sales process including, at least, improved measurement capabilities, matching the foot to particular footwear, and the footwear design process, the footwear manufacturing process.

SUMMARY OF THE INVENTION

A method is provided for measuring bottom facing surfaces of foot which comprises the steps of placing a foot against a reference surface within the scanning field of the scanner, scanning bottom facing surfaces of a foot, and electronically displaying the scan of the foot bottom facing surfaces on a visual display to produce a scanned foot image articulating distances of portions of the foot bottom facing surface from the reference surface. The electronically displaying step may further include assigning gray scale values to distances articulated to produce a scan foot image comprising more than two gray scale intensities so that a grey scale image with a stereoscopic appearance is provided. Alternatively, the electronically displaying step may include assigning color hues to the distances articulated to produce an image comprising more than two spectral hues so that a color image with a stereoscopic appearance is provided. In addition, a method is provided for measuring bottom facing surfaces of the foot which includes a step of electronically displaying the scan of the foot bottom facing surfaces on a visual display to produce a scan foot image distinguishing regions of the foot bottom facing surface exerting different pressures against the reference surface and assigning grey scale or color values to the foot pressure regions. In addition, a system for topographically mapping bottom facing surfaces of a foot is provided.

BRIEF DESCRIPTION OF THE DRAWINGS

FIG. 2 is a block diagram showing a preferred embodiment of the present electro-optical foot scanner system.

FIG. 3 is a block diagram showing a detailed depiction of the elements of the preferred embodiment central computer.

DETAILED DESCRIPTION

Detailed preferred embodiments of the present invention are disclosed. It is to be understood, however, that the disclosed embodiments are merely exemplary of the invention, which may be embodied in various forms. Therefore, specific structural and functional details disclosed are not to be interpreted as limiting, but rather as a representative basis for teaching one skilled in the art to variously employ the present invention in virtually any appropriately detailed system or structure.

Figure 1:
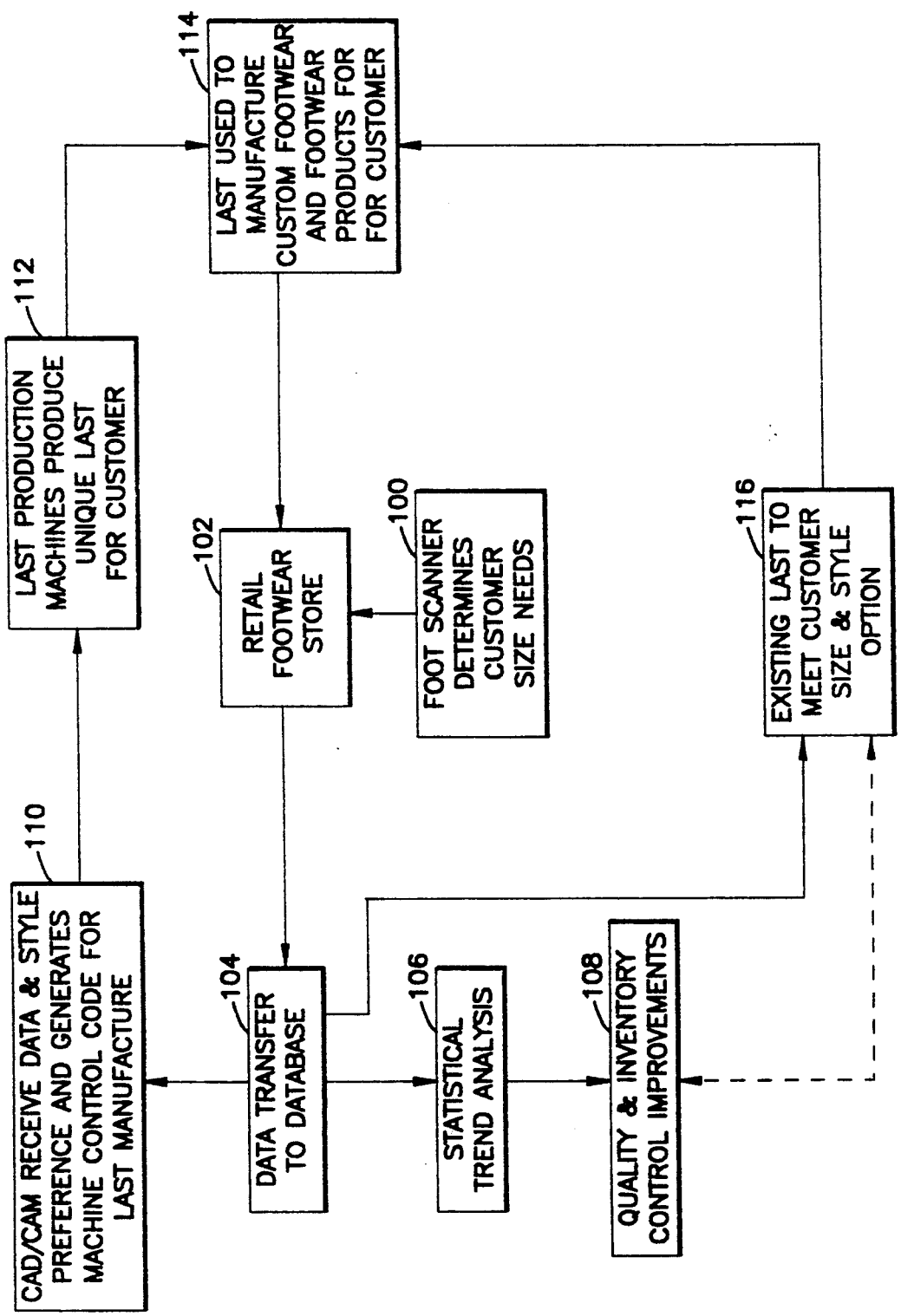
FIG. 1 is a block diagram showing a generalized diagram of the present computerized system.

Referring now more particularly to FIG. 1, which is a block diagram showing a generalized diagram of the present computerized system. The present computerized system encompasses a preferred footwear manufacturing environment from the retail store outlet through the manufacturing process and back to the retail footwear store. In particular, within the preferred retail footwear store 102, an electro-optical foot scanner unit 100 would preferably be placed to determine customer footwear size needs. Foot scanner unit 100 would derive a three-dimensional topographical image of a particular customer's feet. From the electronically derived topographical image of the feet, a foot size is electronically computed. The foot size could be assigned according to any foot sizing method including, for example, the Brannock measuring system, the TWAC ™ measurement system and others. Foot measurement information for the particular customer would be stored in a database for a later transference to a centralized database. After determining the particular size of footwear required for the customer, a substantially instantaneous electronic query can be made by way of a computing device into electronically stored inventory data to determine if such a size is available of the desired footwear to provide to the particular customer.

By way of example, the following will describe the procedures for transferring the foot sizing information of a particular customer to the manufacturing facilities so that custom fit footwear can be made and subsequent transference of that finished product back to the retail footwear store is accomplished. After electro-optical scanning of the particular customer's feet with foot scanner 100, information is transferred to a central storage facility for a particular retail footwear store 102. Subsequently, such information is electronically transferred to a centralized database 104 by way of one of several communication methods including a computerized network transfer, serial data communication, parallel data communication, and modem communication or by transferring a storage medium such as a floppy disk, magnetic tape, optical disk, punch tape, punch card, or other storage medium readable by an electronic computing means. Once the customer foot size information is in the centralized database 104, a query into an existing footwear last database 116 is checked electronically for a last which could be used to manufacture a custom fit piece of footwear for the particular customer. In the preferred embodiment, information would be stored on all lasts kept for use in manufacturing particular footwear according to size and style. In querying the existing last database 116 with sizing information for the particular customer, lasts preferably would be selected which closely match the particular customer's needs as well as lasts which exactly match the particular customer's needs. If it is determined that a last exists which would be useable for the particular custom footwear, information can be transferred to footwear production facilities 114 so that the chosen last can be used to manufacture custom fit footwear and other footwear products for the customer. Custom footwear products could include items such as custom fit insoles, heel cups, metatarsal support, volume adjustment shims, and the like. Custom footwear could include boots, shoes, and other various forms of footwear.

If a last which would produce footwear fitting the particular customer is not found in the existing last database 116, the foot measurement information for the customer can be transferred to a CAD/CAM machine 110 which electronically receives the scanned feet data and style preference information. From the received data the CAD/CAM machine 110 generates machine control code for producing a last. Once the machine control code is generated, the information may be transferred electronically or otherwise to a last production machine 112 which can produce a unique last for the customer. After producing the unique last for the customer, the last can be transferred to the footwear manufacturing facilities 114 so that custom footwear and footwear products can be manufactured for the customer. In the preferred embodiment, the manufactured footwear and footwear products can then be sent to the retail footwear store 102 for delivery to the customer. The unique last may also be transferred to the retail footwear store for storage at the retail footwear store or delivery to the customer so that the customer can save the last for subsequent manufacturing of custom footwear and footwear products.

Centralized footwear database 104 also has links to a mechanism which can perform statistical trend analysis 106 for determining such information as may be desired. Some of the statistical trend analysis may include particular styles or sizes of styles which are requested frequently by customers as well as which lasts are the best lasts to store for subsequent use in manufacturing products for other customers. Thus, by providing improved statistical analysis of actual feet, it is possible to more efficiently "nest" the last production itself. For example, such "nesting" may occur due to phenomenon such as gender, occupation, geography, ethnic background, or other diverse characteristics. In addition, the statistical analysis mechanism 106 can transfer the information to quality and inventory control mechanisms 108 so that improvements in the styles and sizes of existing lasts used in mass production of footwear can be made if desirable by modifying the information stored in the existing last database 116. Substantial last and footwear inventory reductions are possibly utilizing this improved method of last inventory management.

Referring now more particularly to FIG. 2, a block diagram showing the preferred embodiment of the present electro-optical foot scanner system 100 is shown. In the preferred embodiment, a central computing device 120 controls operations of several peripheral devices. Display 122 is coupled to central computer 120 so that information which is received by the central computer may be displayed for viewing by a user. Display 122 in the preferred embodiment includes an electronic video display capable of reproducing images consisting of a plurality of hues and shades of color.

In addition, central computer 120 is coupled to inventory data 124 which can be stored in storage device 130 or in other storage devices proximate foot scanner unit 100. Inventory data 124 includes information concerning number of footwear available at retail footwear store 102 in particular styles and sizes. Further inventory data 124 may include information which indicates all footwear styles and sizes available from a footwear manufacturer 114 at a particular retail footwear store 102 on request, or other information.

Input device 126 provides means for obtaining information from a user and supplying such information to central computer 120. Input device 126 may include many types of electronic input devices including a keyboard, mouse, track ball, light pen, electronic tablet, and touch screen, voice recognition unit, or other devices. It will be appreciated by those skilled in the art that improved input devices may be substituted for use in the preferred embodiment as they are developed. In the preferred embodiment, foot scanner unit 100 is optimized for use with a combination of keyboard and touch screen input devices. These input devices are used to select menu choice options presented on display 122 as well as input and retrieve information used by central computer 120.

A storage device 130 is coupled to central computer 120 for local storage of information received by central computer 120. Storage device 130 may be configured in several forms including combination of tape drives, hard disk drives, floppy disk drives, optical disk drives, static ram or other electronic storage devices. It will be appreciated by those skilled in the art that the particular storage device used will be highly dependent upon the performance characteristics desired for use in the particular environment in which the foot scanner unit is to be utilized. In the preferred embodiment, a hard disk drive is utilized for local storage of information.

Figure 3A:
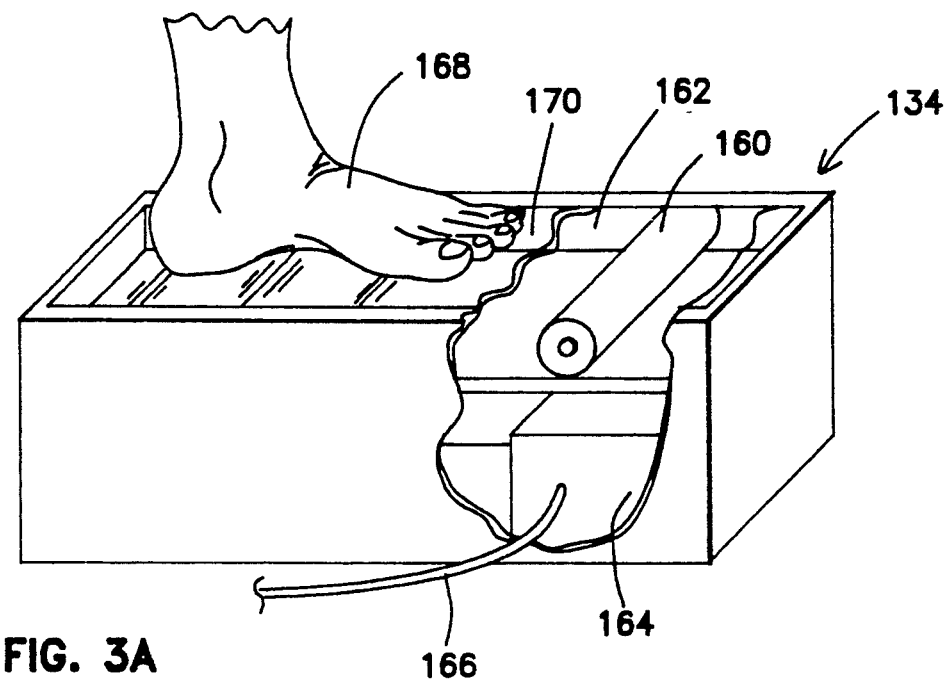
FIG. 3A is a block diagram showing a detailed depiction of the elements of the preferred embodiment electro-optical foot scanner.

A scanner unit 134 is coupled to central computer 120. The scanner unit 134, as will be further detailed in FIG. 3A, provides a three-dimensional, topographical electronic image of a foot which has been scanned. In other words, the scanner unit 134 provides precision contour mapping of bottom surfaces and substantially bottom facing surfaces of a scanned foot. Particular topographical information concerning a particular foot may be derived by determining the intensity of lightness and darkness of portions of the scanned foot image with respect to other portions of the scanned foot image. In particular, image portions which are generally lighter in color or intensity are designated as being closer to the scanner unit than portions of the foot which are darker in color or intensity. Further, parts of the foot which actually touch the surface of the electro-optical scanner 134 are all the same distance from the surface of the scanner; however, the color of the scanned foot still varies. For example, the color of the surface of the foot pressed against the surface of the scanner 134 may vary according to the amount of pressure applied to the surface of the scanner unit in direct correlation to the amount of blood flowing through the foot surface at that particular point. In this case, foot surfaces under extreme pressure will be lighter in color hue than foot surfaces under less pressure which will be generally pinkish or skin tone in color. By further defining the topographical image of the scanned foot which is in contact with the surface of the scanner 134 to include variations according to foot surface color, a more accurate image of the scanned foot is formed.

In addition, the foot scanner 134 may be adjusted to accommodate a foot with light skin tone, dark skin tone, a white sock, or even a dark sock by varying the intensity of the light source used in the electro-optical scanning process which is directed at the foot being scanned. It will be appreciated by those skilled in the art that improved scanner units may be substituted for use in the preferred embodiment foot sizing system without departing from the teachings of the present invention. More particularly, alternative methods of obtaining topographical information on a foot may be utilized such as laser-optic scanners, CAT scanners, pressure plate scanners, resistive force plates, nuclear magnetic scanners, acoustic-based scanners, variable height pin and electromechanical array based scanners, or other three-dimensional measurement devices in place of the preferred embodiment electro-optical scanner.

In an alternative embodiment, a printer 128 may also be coupled to central computer 120 so that hard copy of information which has been displayed on display 122 may be provided to a user or customer. In addition, the information stored and manipulated by central computer 120 may also be provided to statistical analysis tools 132 for use in computing optimum retail store inventory of footwear, ordering more inventory of footwear, determining the most popular styles of footwear, or other various statistical analysis which may utilize information already stored through central computer 120.

Referring now more particularly to central computer 120, as detailed in FIG. 3. Central computer 120 preferably includes several optimized elements for manipulating and interfacing with externally coupled devices. Central computer 120 is generally operated through a central processing unit (CPU) 142 which is logically coupled to a central bus 140. Bus 140 passes data between all of the elements of central computer 120. By way of bus 140, CPU 142 communicates with a scanner basic input/output system (BIOS) 144 which is in turn coupled through bus 140 to a small computer system interface (SCSI) 150 operatively interconnected to the scanner. BIOS 144 provides instructions to the scanner during the scanning process and helps control the flow of information to and from the scanner.

CPU 142 further communicates through bus 140 to video controller 146 which is operatively interconnected to the display or monitor. Video controller 146 generates display screens compatible with the monitor from information provided by CPU 142. Such information may include an electronically enhanced scanned image of a customer's foot, footwear catalog information, pricing, and retail footwear store inventory.

The electronically enhanced scanned image preferably is displayed in a plurality of colors or shades of a single color. Preferably, those portions of the scanned foot image which have been determined to be closest to the scanner 134 surface by central computer 120 are assigned the colors of lightest hue or shades of a single color of highest intensity. In addition, the portions of the foot surface deemed to be furthest away from the scanner 134 surface by central computer 120 are assigned colors of darker hues or shades of a single color which are darker in light intensity than those assigned to portions of the foot which were deemed closer to the scanner 134 surface by central computer 120. It will be appreciated by those skilled in the art that the shades of a color or a plurality of colors may be assigned in a variety of different manners while precisely depicting the topographical contours of the foot. The present invention should not be limited to the particular colors or shades of color assignment schemes detailed hereinafter.

Figure 8:
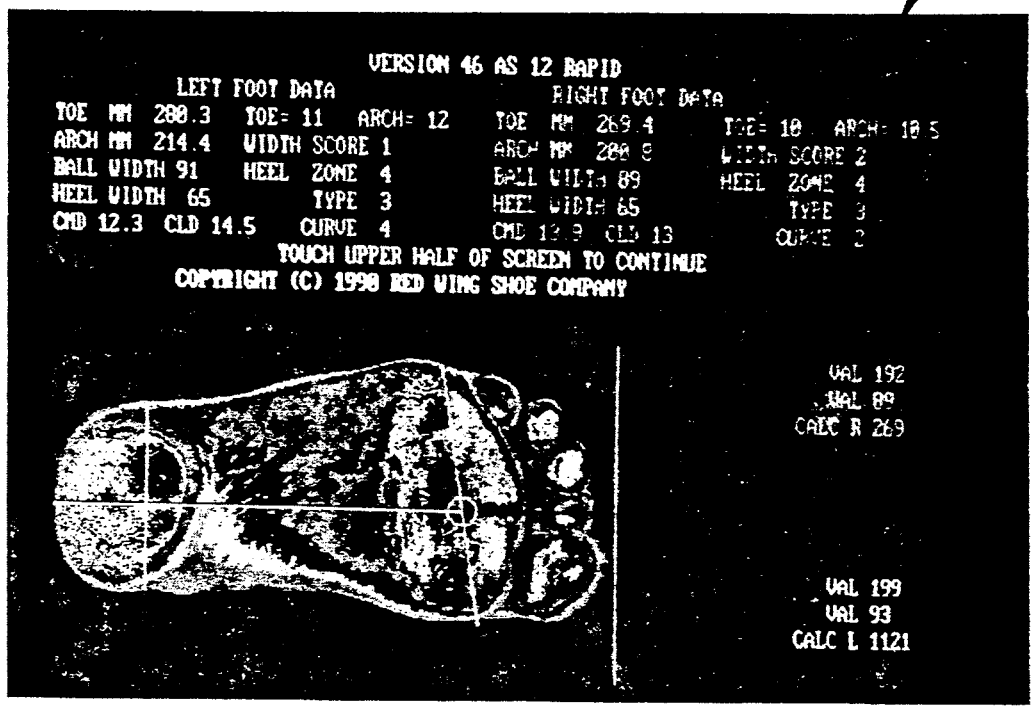
Figure 9:
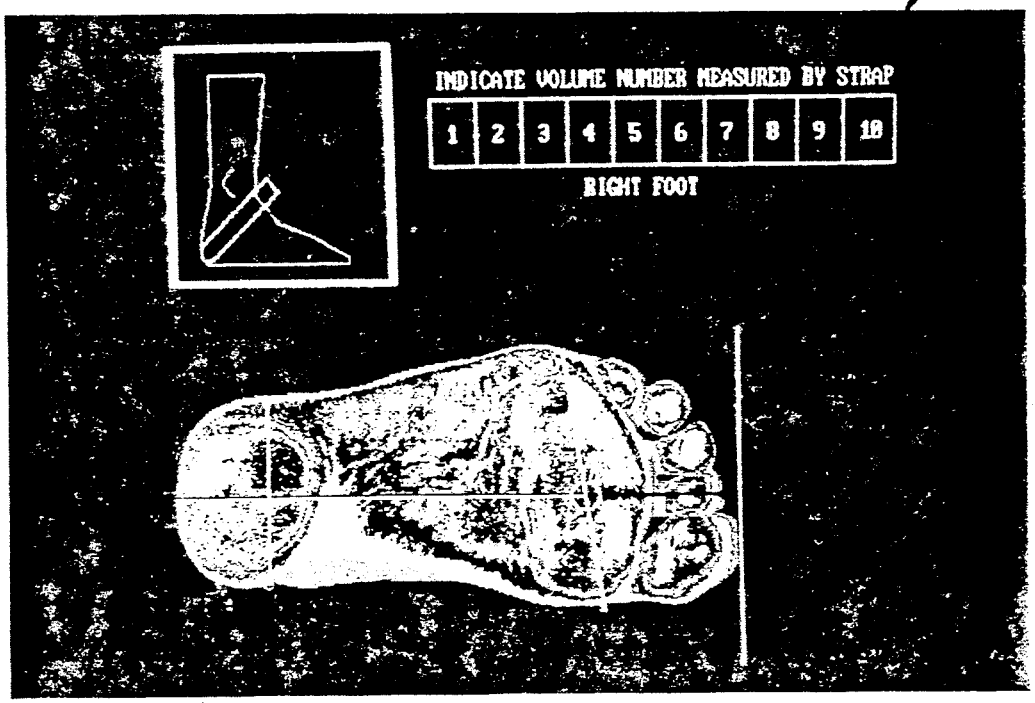

For example, in the preferred embodiment, a scanned foot image, such as the one shown in FIGS. 8 and 9, has a stereoscopic appearance due to the assignment of shades of gray which are lighter or darker based on distance of the foot from the scanner 134 surface. In particular, lighter shades of gray have been assigned to the bottoms of the toes and heel which are under higher pressure due to the weight of the owner of the foot than the surrounding areas which are also touching the scanner 134 surface. Similarly, the portions of the scanned foot which are not touching the surface of the scanner are also assigned lighter shades of gray if those portions are nearer the scanner 134 surface than the surrounding areas which are not touching the scanner 134 surface. It will be appreciated that a similar light to dark assignment of scheme can be applied if a color display were utilized such that colors which correspond to lighter or more bright hues could be assigned to the foot image portions which are to appear closer than foot image portions which are to appear as if they are farther away. This assignment of shades of gray and colors is in accordance with the natural perceptive techniques that the human eye uses to assign depth to a two-dimensional image it is viewing. Further, it will be appreciated that numerous modifications to the assignment of shades and color hues presented on the display 122 for a foot image can be made without departing from the scope of the present invention.

CPU 142 is further coupled through bus 140 to serial input/output interface 148 which provides a communication port through which input devices, preferably including a keyboard and touch screen may provide information to CPU 142. In addition, serial input/output (I/O) device 148 is operatively interconnected to remotely located inventory data 124 via a local area network, modem or other form of serial communication.

The remotely located inventory data 124 may be stored within centralized database 104. CPU 142 is operatively interconnected through bus 140 to specialized micro-chip controllers which improve the performance of central computer 120 by reducing the demands on CPU 142. These specialized chips include a math co-microprocessor 156 and direct memory access (DMA) controller 154. Math co-microprocessor 156 alleviates much of the computational demand placed on CPU 142 for the graphic intensive operations of central computer 120 thereby allowing CPU 142 to work on other tasks more efficiently. DMA controller 154 also alleviates part of the data manipulation load placed on CPU 142 by controlling data access to relatively slow data storage devices such as the storage devices connected to hard disk controller 158 and data being received from serial I/O device 148 as well as SCSI controller 150.

In an alternative embodiment, a parallel input/output device controller 152 is included in central computer 120 for controlling communications through bus 140 to CPU 142 which are from a printer or other external device using a parallel input/output interface.

Referring now more particularly to FIG. 3A which shows a detailed depiction of the elements of a preferred embodiment electro-optical foot scanner 134 includes an optical scan head 160 which moves along a fixed track 162 during the scan process. Scanner 134 also includes a control unit 164 which adjusts the light intensity of the optical scan head 160, the speed at which the optical scan head 160 moves within track 162 during scanning operations, and the flow of data to and from central computer 120 which is coupled to scanner 134 through logical connection 166. Scanner 134 also includes a planar reference surface 170. Other shaped reference surfaces may be substituted for planar reference surface 120 without departing from the teachings of the present invention. For instance, a reference surface generally formed such that it conforms to the bottom surface of a foot may be utilized. During a typical scanning operation a foot to be scanned 168 is placed on one side of reference surface 170 such that the bottom facing surfaces of the foot 168 are proximate the reference surface 170. Optical scan head 160 moves along track 162 along the other side of reference surface 170. In the preferred embodiment control unit 164 consists of a Tokyo Electric Company, Limited optical scanner engine which provides a reference surface which is large enough to accommodate foot sizes up to twenty according to the Brannock measuring system or more specifically 520×220 pixel resolution where each pixel is 5 mm square. In addition, the Tokyo Electric Company, Limited engine allows adjustment of the light source intensity used in conjunction with the optical scan head including eight levels of brightness and six levels of contrast. In addition the Tokyo Electric Company, Limited engine provides relatively quick optical scan head movement and therefore relatively quick scanning of the bottom facing surface of foot 168. Further, the central computer 120 includes computational elements for deriving a level heel to foot length, foot width, arch-line, and foot curvature measurement from the data received from foot image data received from scanner 134. It will be appreciated by those skilled in the art that other scanners may be substituted for the particular scanner specified above which meet or exceed the particular specifications of the Tokyo Electric Company, Limited scanner engine.

Figure 4A:
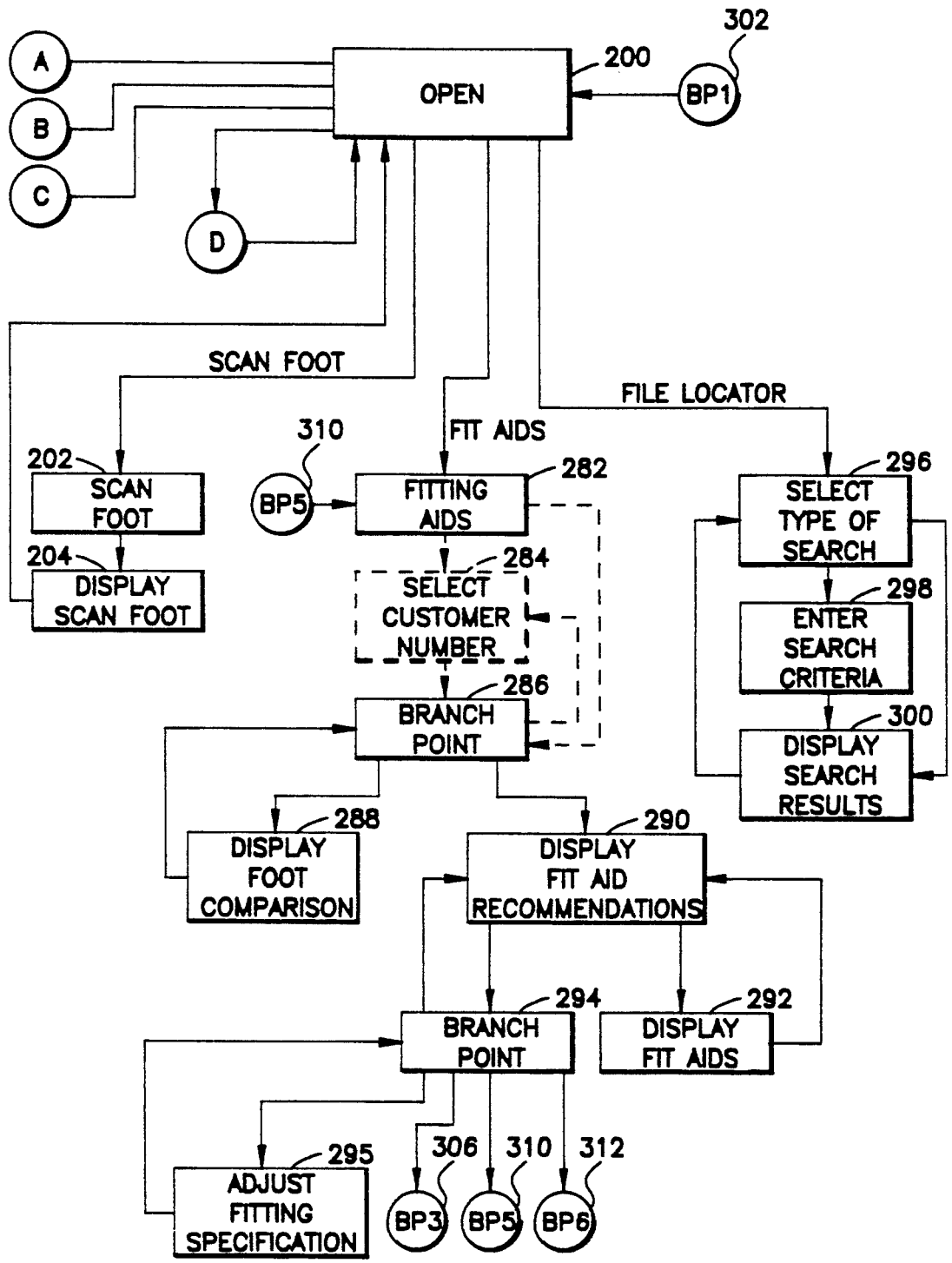
FIGS. 4A, 4B and 4C show a flowchart diagramming an example of operating a preferred embodiment electro-optical foot scanner unit from a user's point of view.
Figure 4B:
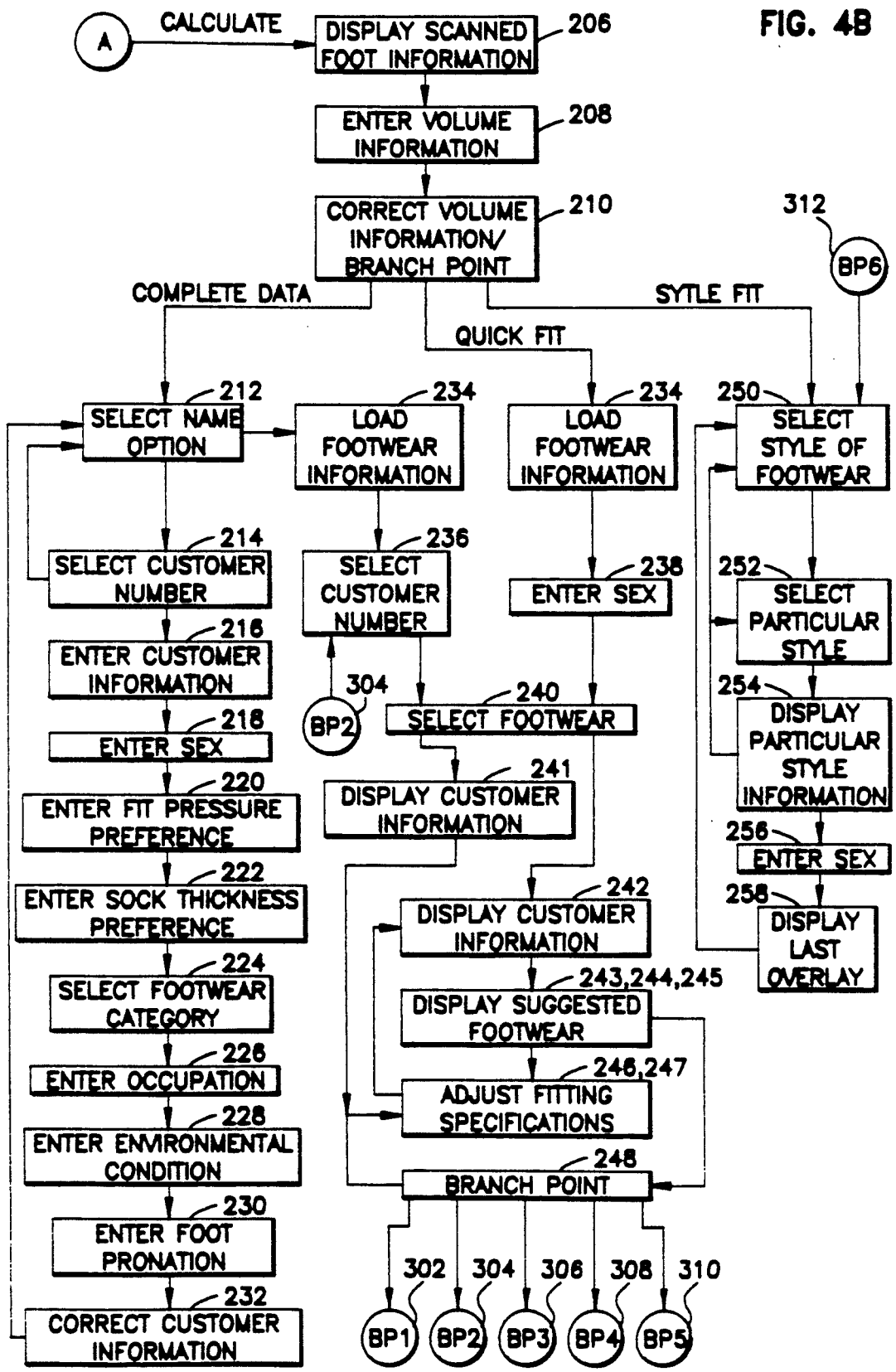
Figure 4C:
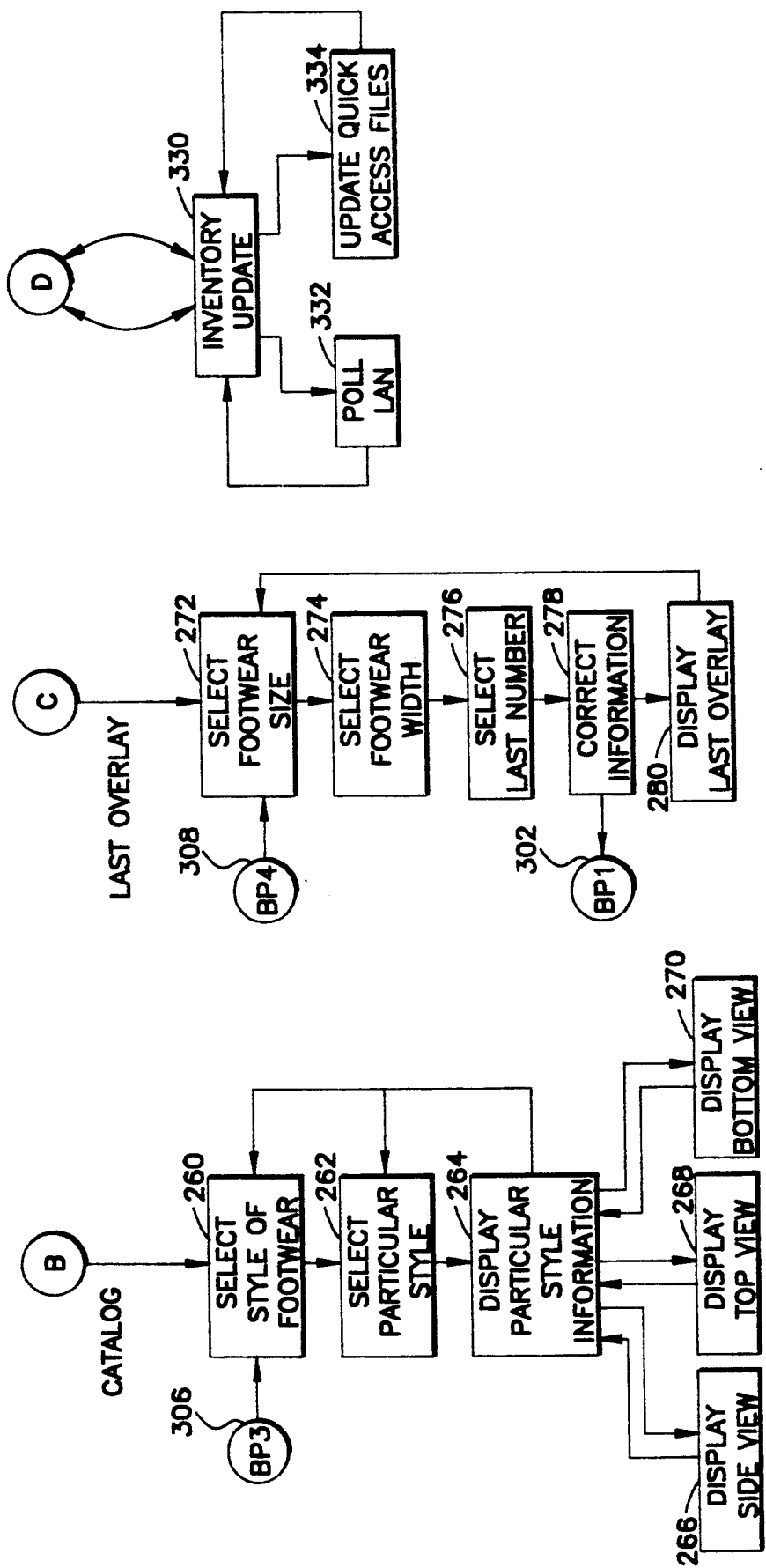

Referring now to FIGS. 4A, 4B, and 4C, these figures encompass a flowchart of an example showing the use of the preferred electro-optical foot scanner unit, shown in FIG. 2. The flowchart diagram is an example of using electro-optical foot scanner unit from a user's point of view by depicting graphical and textual information which may be shown to a user. This information preferably is shown to a user on a video display screen for review and/or for providing continued navigation through a series of display screens.

Referring now more particularly to FIG. 4A, by starting at the open menu/screen display 200 (shown in FIG. 6) a user is given a choice to select from a plurality of options including an option to go to a scan foot menu/screen display 202. Upon selecting with an input device 126 (hereinafter referred to as selecting) either scan left foot or scan right foot options from open menu/display screen 200, a scan foot menu/screen display 202 such as the one shown in FIG. 7 is presented on the display 122. At this point a user may choose to select scanning of foot which is bare, which has a light sock, or which has a dark sock. After selecting a foot scanning option, a foot is scanned by scanner 134. As the foot is scanned, the information is processed by central computer 120 and the scanned foot image 204 is displayed on display 122. Preferably, as the scanner scans through the length of a particular foot proximate scanner 134, display screen 204 (not shown) displays the portion of the particular foot which has already been scanned. By displaying the image of the scanned foot or screen display 204 as scanner 134 scans the particular foot, a user will focus their attention on the scanned image rather than the length of time that it actually takes to scan the foot, thereby causing the scanning of the foot to be relatively quick from a user's point of view. After scanning and displaying the scanned foot image, open menu/screen display 200 is presented to the user once again. After scanning both the left and right foot in a substantially similar manner as described above, the user may choose to calculate information about the scanned feet.

Referring now more particularly to FIG. 4B, upon selecting to calculate the feet information, display scanned foot information menu/screen display 206, shown in FIG. 8, is presented on display 122. Menu/screen display 206 displays information about each of the scanned feet including Brannock foot sizes and TWAC TM foot sizes. Menu/screen display 206 further displays an image of the scanned foot which contains overlaid highlight lines including a heel to toe length highlight, center line highlight, heel width highlight, ball width highlight and T point circle highlight. The TWAC TM measurement system includes calculating a length measurement from a foot centerline from the heel to toe, a width line between medial and lateral portions of the foot or between flexion points, an arch-line type, and the angle of curvature of the medial edge and the lateral edge of the foot as determined from a heel point at the base of the heel. Also included in the TWAC ™ foot sizing measurement system are calculations of heel width and foot volume.

Figure 10:
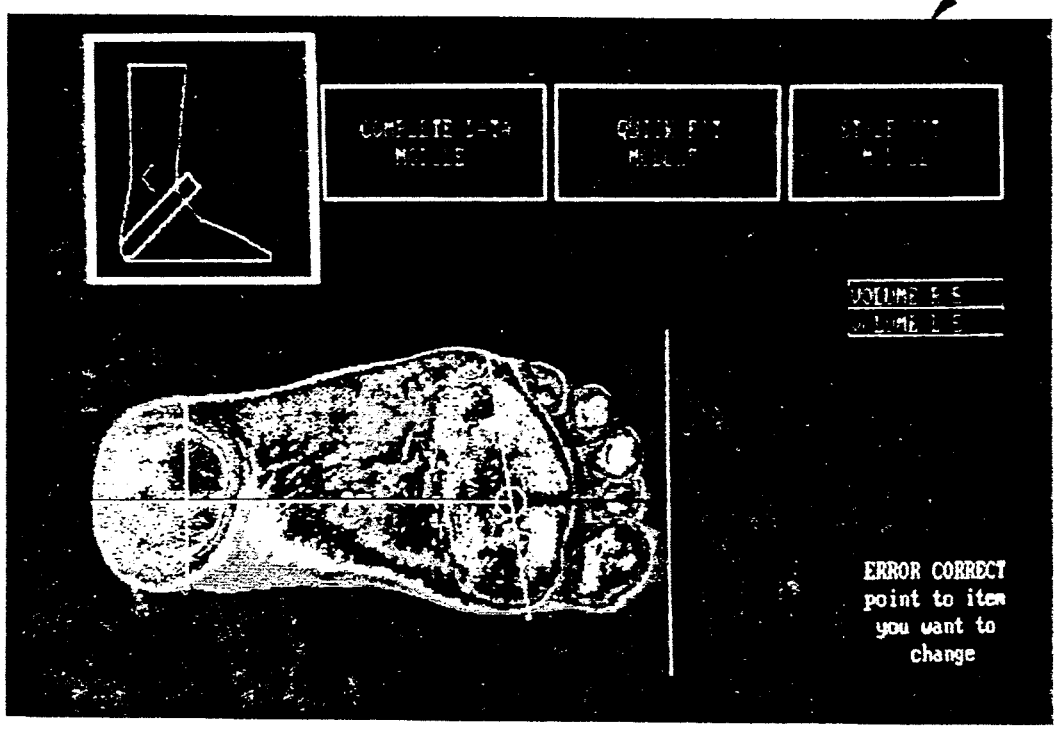

Upon selecting to continue entering information about each foot, enter volume information menu/screen display 208, shown in FIG. 9, is displayed on the screen display 122. In an alternative embodiment, the volume information may be automatically measured by the scanner unit and entered into the center computer. A user is prompted to enter a volume number measured by a strap wrapped from the heel to the instep of the foot. After entering the volume information, menu/screen display 210, shown in FIG. 10, is presented on display 122. A user may select from a plurality of options including correcting volume information or branching to three other software program modules including complete data module, quick fit module, style fit module. If a user chooses to correct volume information, menu/screen display 208 is presented on display 122 for the particular foot selected.

Figure 11:
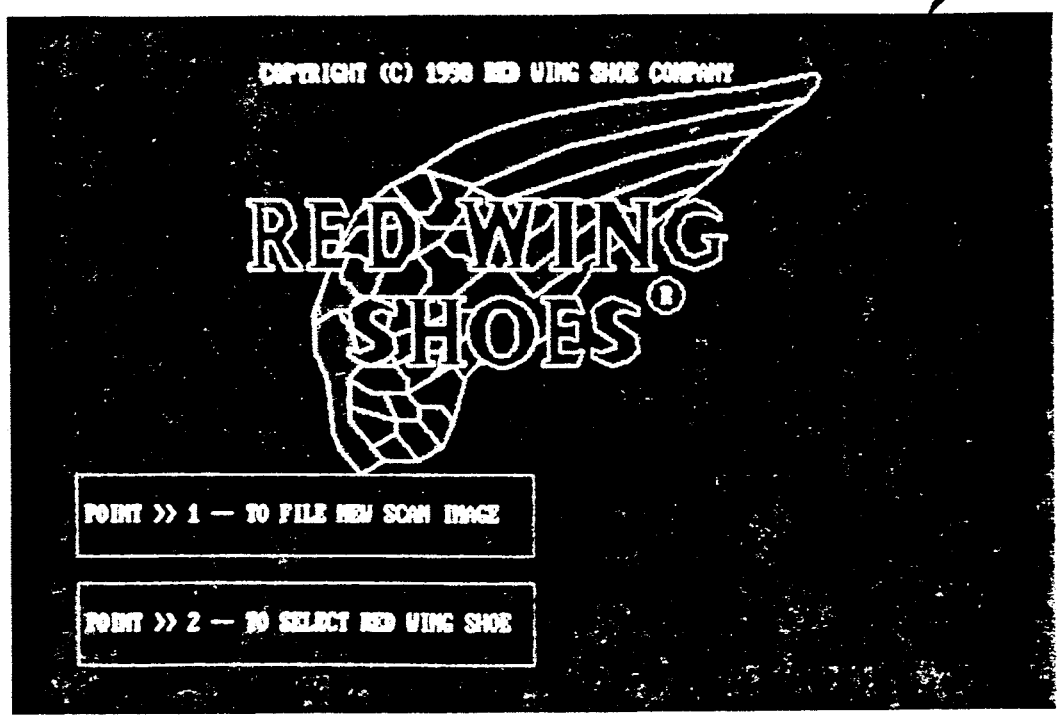
Figure 14:
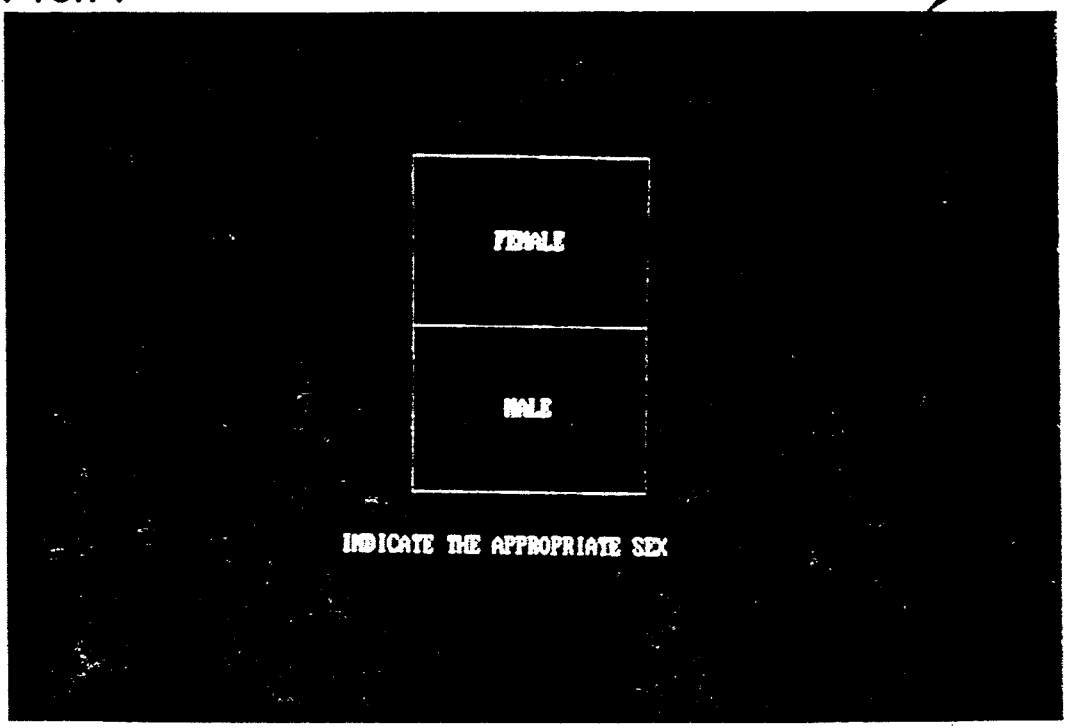
Figure 15:
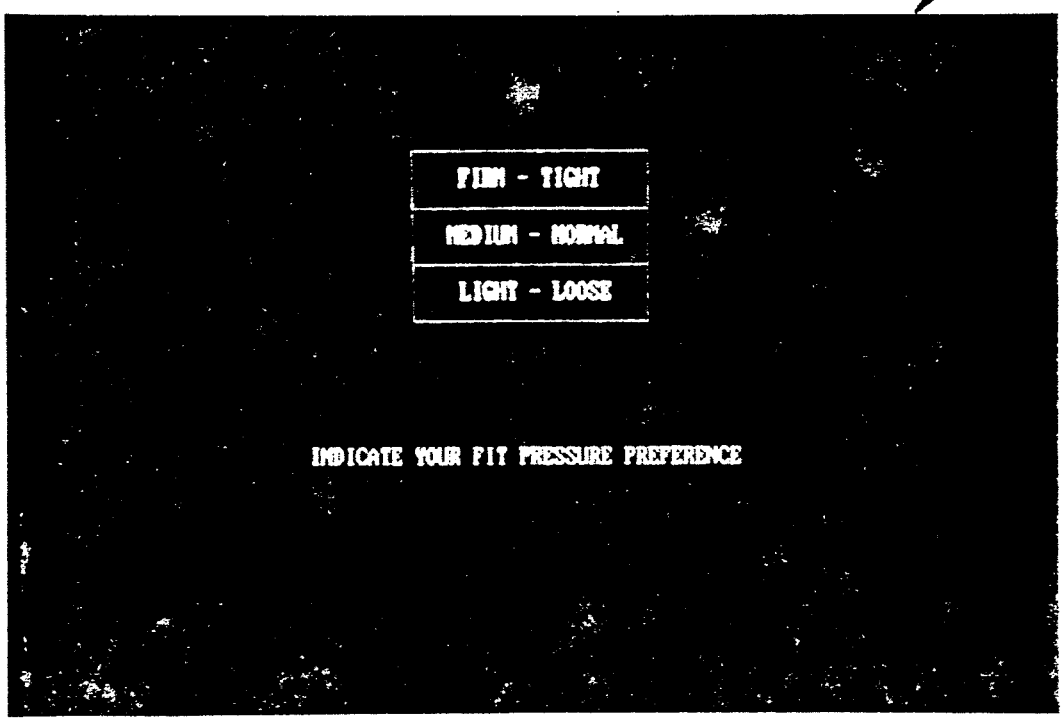
Figure 20:
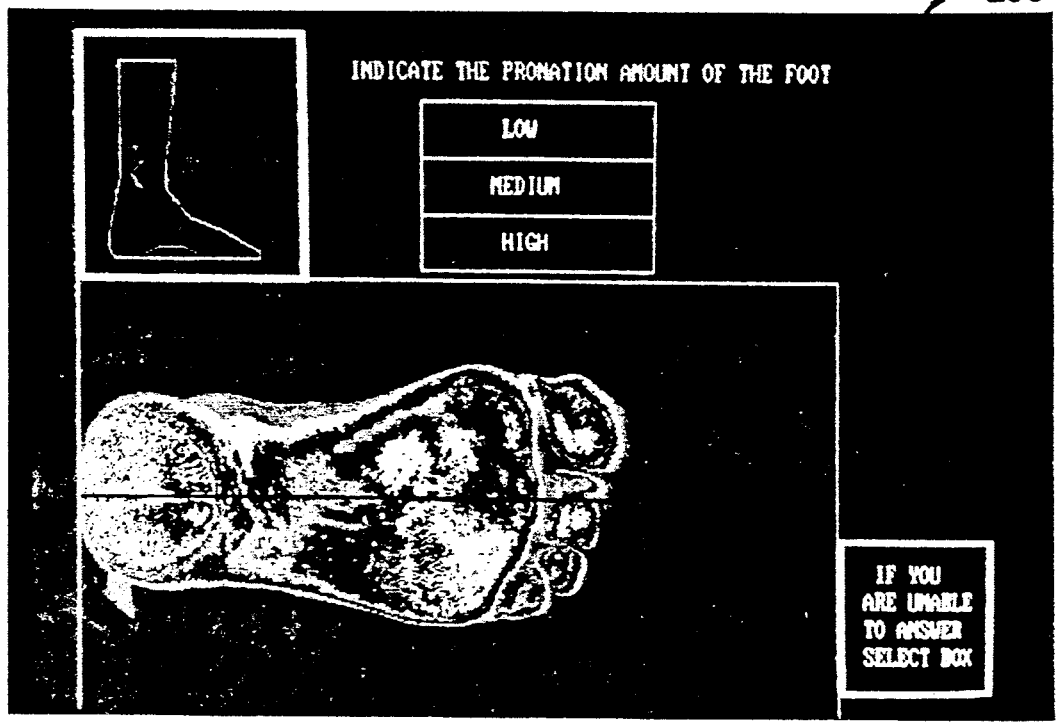
Figure 21:
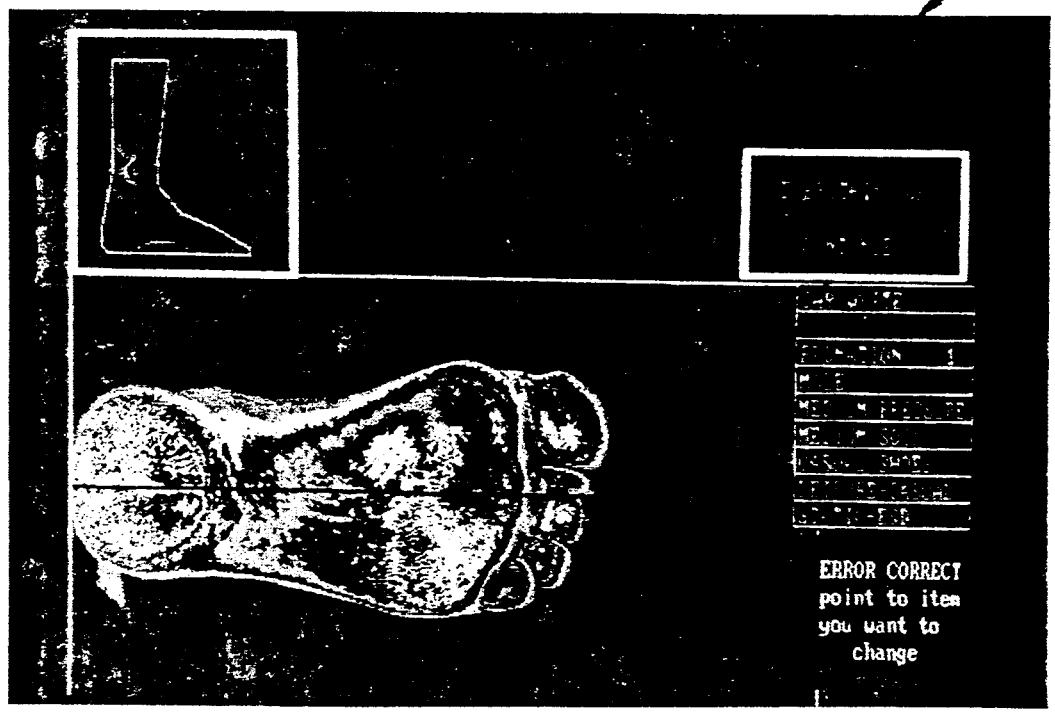

Upon selecting the complete data module, select name option menu/screen display 212, shown in FIG. 11, is presented on display 122. Upon selecting to attach the foot scan image information to a file, menu/screen display 214, shown in FIG. 12, is presented on display 122. A user selects one of five available current customer files to save the customer information under. Upon selecting a particular current customer file to save the scanned foot image information under which automatically assigns new input to a storage file in storage device 130, menu/screen display 216, shown in FIG. 13, is presented on screen display 122. The display screen keyboard prompts the user to input a customer name, address, phone number and age by selecting the characters on menu/screen display 216. After completing this information, menu/screen display 218, shown in FIG. 14, is presented on screen display 122. After selecting the appropriate customer sex, menu/screen display 220, shown in FIG. 15, is presented on display 122. After selecting the particular footwear fit pressure preference, menu/screen display 222, shown in FIG. 16, is presented on screen display 122. After selecting the customer sock thickness preference, menu/screen display 224, shown in FIG. 17, is presented on display 122. After selecting the particular footwear category which the customer desires to be fitted to, menu/screen display 226, shown in FIG. 18, is presented on display 122. After selecting the particular occupation which the customer plans to use the particular footwear for, menu/screen display 228, shown in FIG. 19, is presented on display 122. After selecting the particular environmental condition in which the footwear would most frequently be worn, menu/screen display 230 is presented on display 122. The user shall review the scanned foot image and select the amount of pronation of the foot or select unable to answer this question and central computer 120 shall determine the amount of pronation. After selecting the amount of pronation of the foot by either method, menu/screen display 232, shown in FIG. 21, is presented on display 122. At this point the user is prompted to check the customer information for errors and correct such information where needed. The information can be corrected by selecting the incorrect information, returning to that particular menu/screen display, correcting the information and returning to menu/screen display 232.

Figure 22:
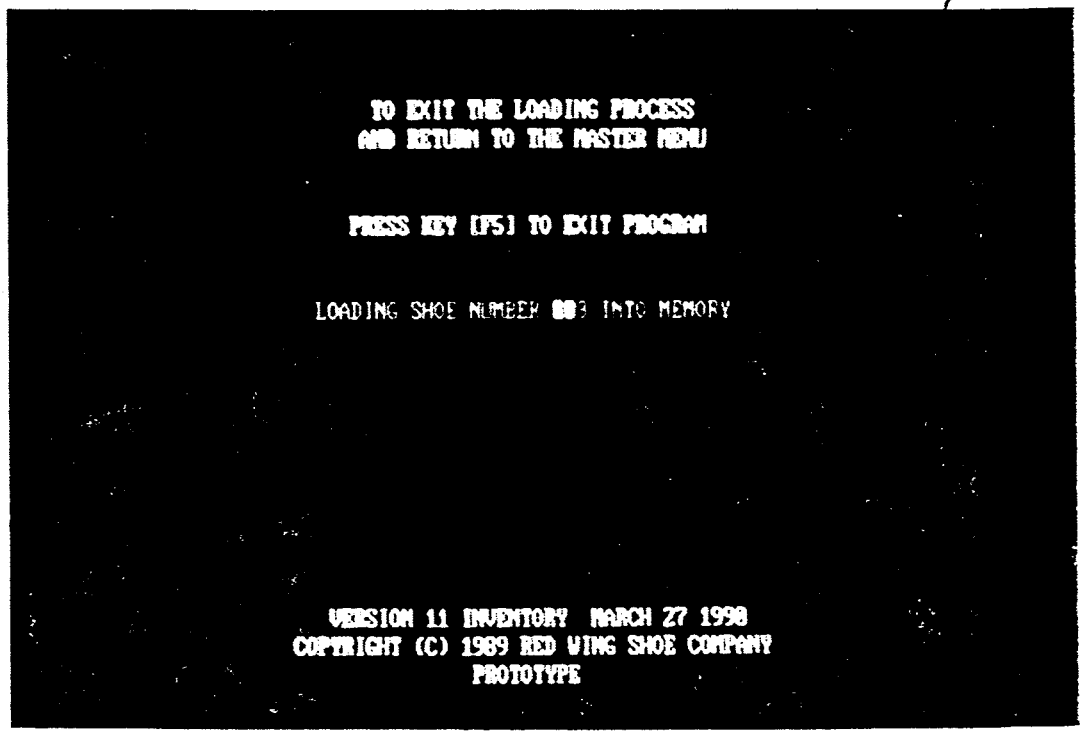

After indicating that all of the information is correct and that program operation should continue, menu/screen display 212, shown in FIG. 11, is once again presented on screen display 122. The user may now choose to select a particular piece of footwear. After selecting to choose a particular piece of footwear, menu/screen display 234, shown in FIG. 22, is presented on display 122. Screen display 234 indicates that central computer 120 is loading footwear information into memory. After loading the footwear information into memory, menu/screen display 236, shown in FIG. 23, automatically is displayed on display 122. Preferably, a user selects one of the current customer files for which to find footwear.

Figure 6:
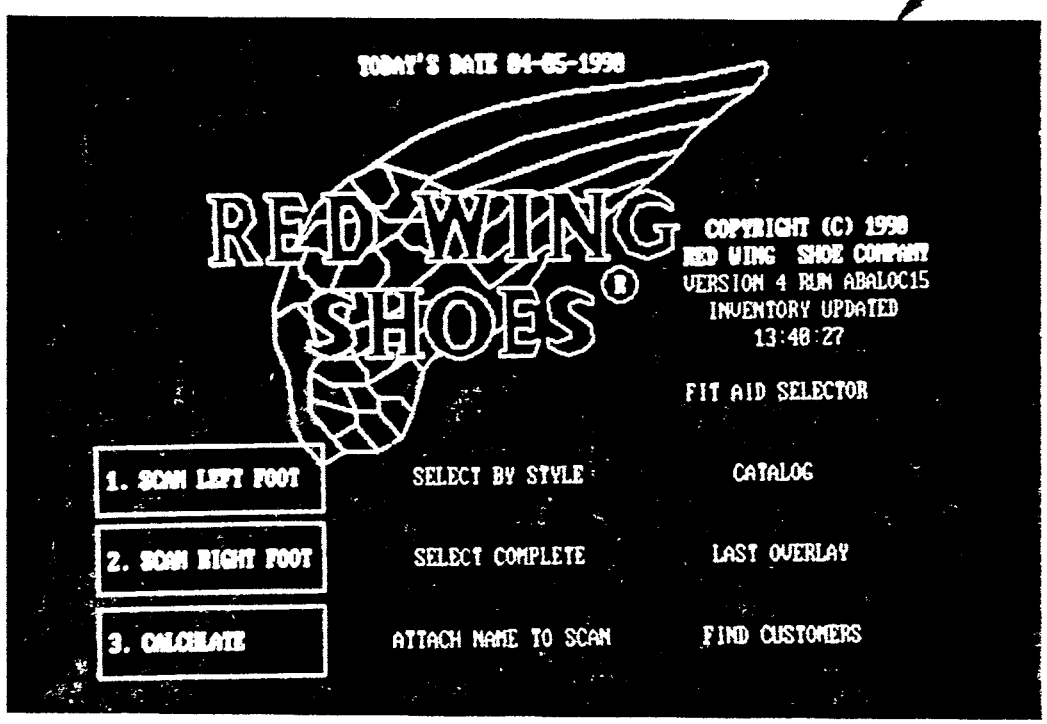
FIGS. 6 through 67 are representations of example menu/screen displays presented to a user during operation of the preferred embodiment electro-optical scanner unit in accordance with the flowchart diagrams, shown in FIGS. 4A, 4B, 4C and 5.
Figure 7:
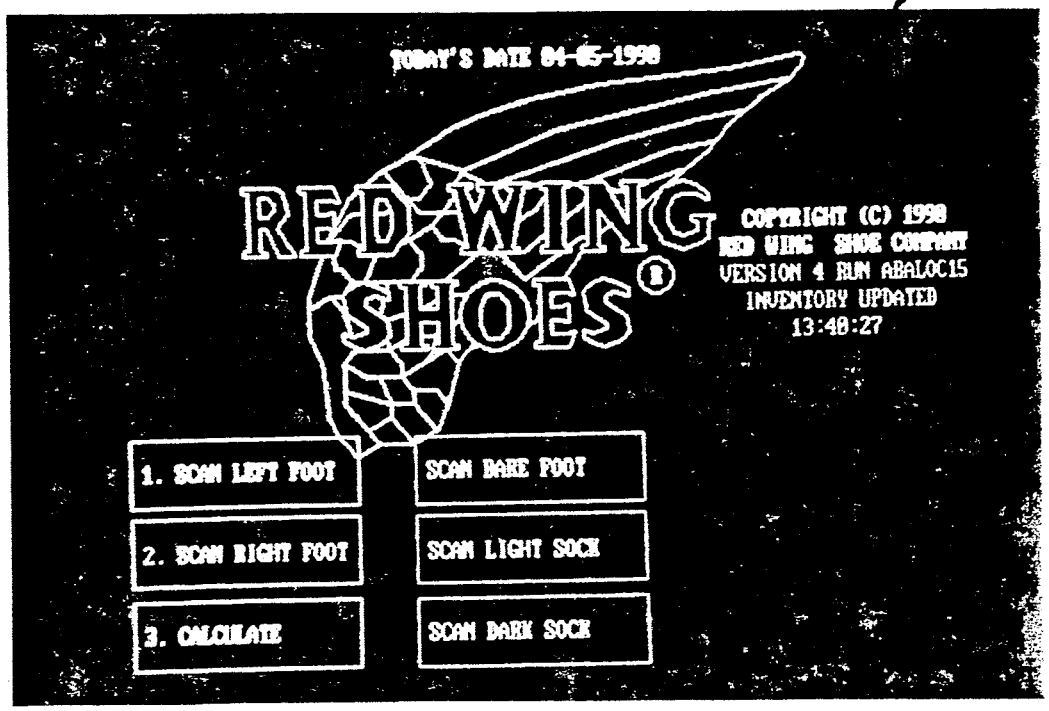

Alternatively, the user may choose to exit this portion of the program and return to menu/screen display 200, shown in FIG. 6. Alternatively, the user may choose to retrieve customer information from a file stored in storage device 130 to use in conjunction with selecting particular footwear. Alternatively, a user may choose to indicate that a quick fit of footwear would like to be accomplished.

Figure 25:
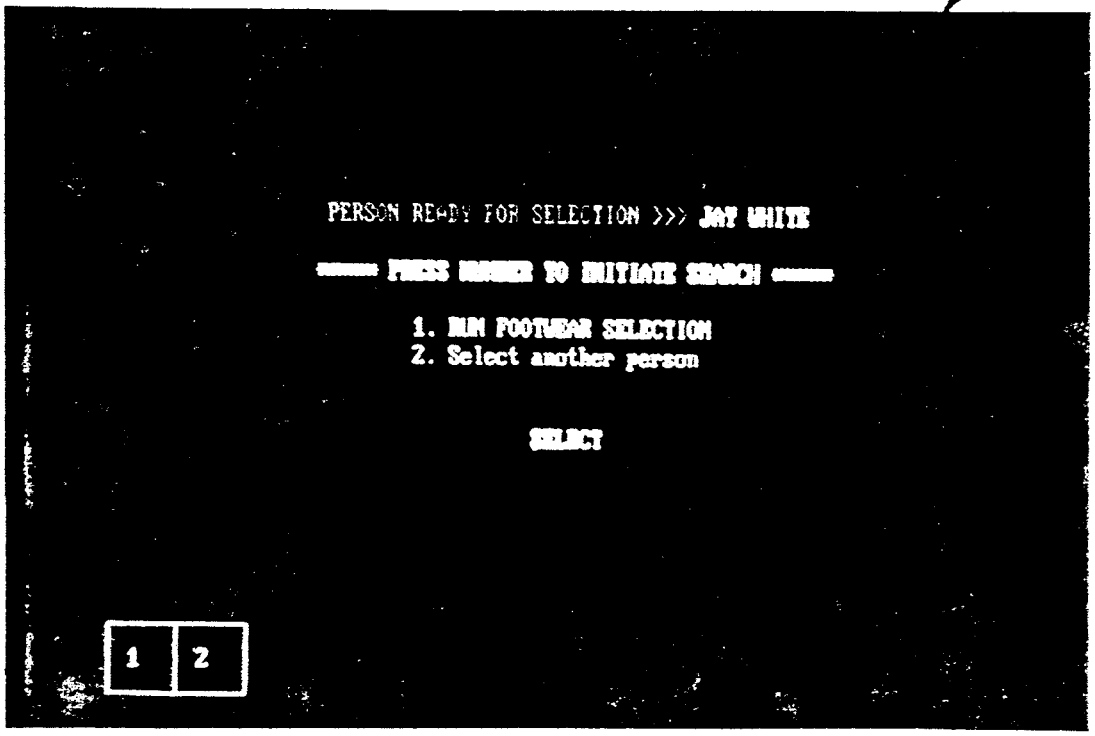
Figure 26:
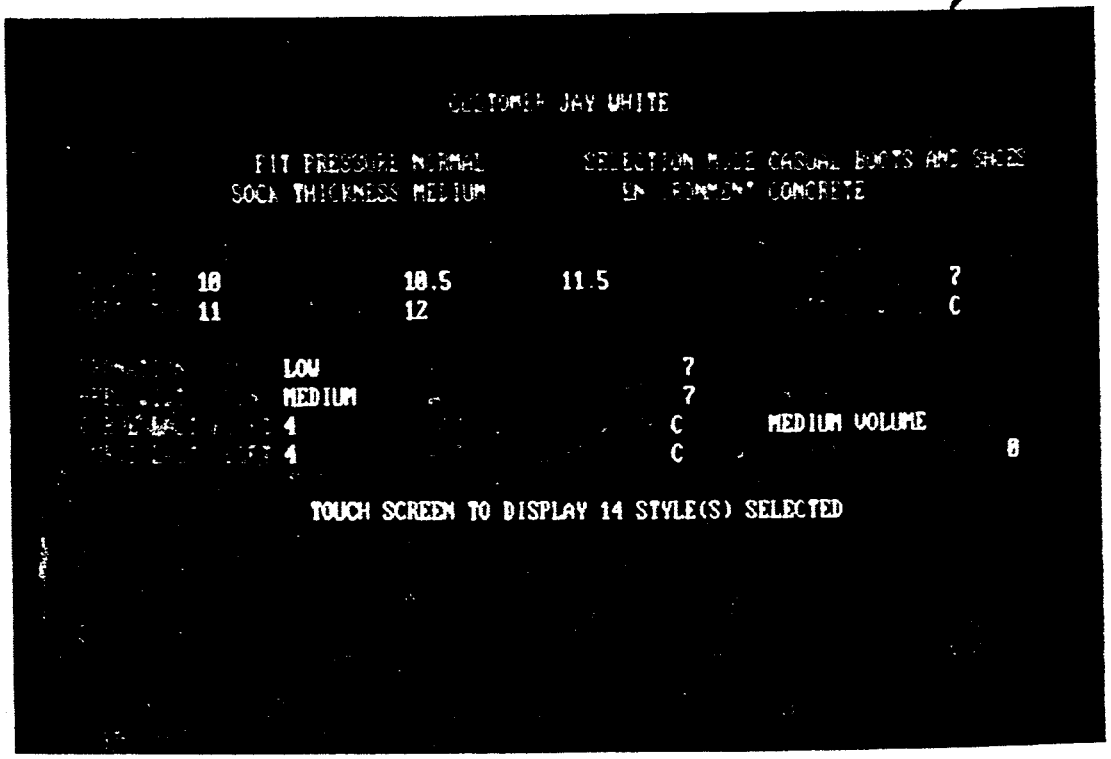
Figure 26A:
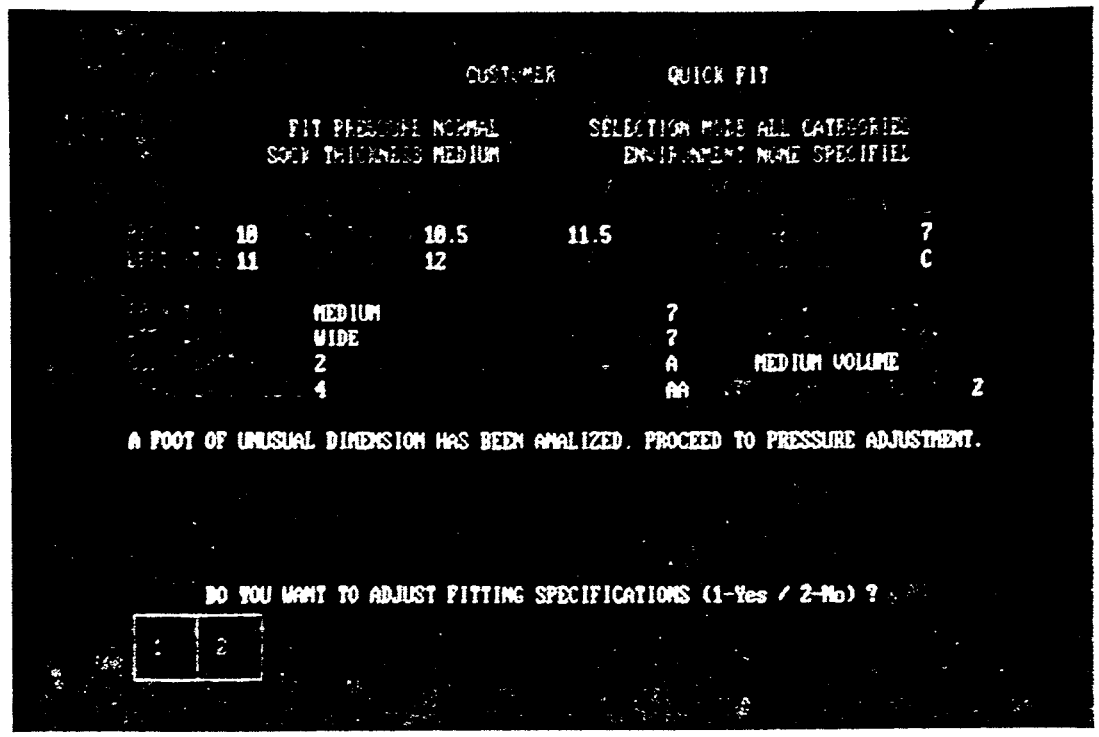

Upon choosing to select particular footwear, menu/screen display 240, shown in FIG. 25, is presented on display 122 wherein the user is prompted to either select another person for which to find footwear and automatically returns to menu/screen display 236 or selects to continue operation by running the footwear selection module. Upon choosing to run the footwear selection module, menu/screen display 242, shown in FIG. 26, is presented on display 122. Alternatively, if central computer 120 determines that a foot of unusual dimensions has been scanned, the user is presented with menu/screen display 241, shown in FIG. 26A, which asks the user to branch directly to the fitting specifications menu/screen display 246, shown in FIG. 30, before recommending footwear for the customer.

A priority assignment and sorting algorithm is used to select footwear models and sizes that match the use categories previously selected by the user. The first seven footwear styles selected by the algorithm are presented on menu/screen display 243, shown in FIG. 27. The items automatically checked for availability in inventory and those which are available are preferably shown in darker (more definite) characters. Similarly, those which are not available in current inventory are preferably displayed in a lighter (less definite) characters. After selecting to view the remaining suggested footwear, menu/screen display 244, shown in FIG. 28, is presented on display 122. The user is asked to select whether or not adjustment to the fitting specifications is necessary. If such adjustments to the fitting specifications are indicated by the user, menu/screen display 246, shown in FIG. 30, is presented on display 122. Within menu/screen display 246, indicators 249 are shown next to particular information categories which central computer 120 has calculated most likely to require adjustment to allow more precise fitting of a customer's foot. Thus, a customer can be prompted to adjust the most likely categories to need adjustment based on the information that central computer 120 has previously been given. Upon selecting a particular category, such as heel width as depicted in menu/screen display 247, shown in FIG. 31, the user is prompted to adjust the fitting specifications. After adjusting the fitting specifications, the user selects to continue program operation and menu/screen display 242, shown in FIG. 26, is presented on display 122.

Alternatively, if from menu/screen display 244, shown in FIG. 28, a user indicates that no adjustments to the fitting specifications are necessary, menu/screen display 245, shown in FIG. 29, is presented on display 122. The user may choose to print a hard copy of the suggested footwear on printer 128. The user may select three different printout formats including complete hard copy of suggested footwear information for footwear in current inventory, only the names of particular suggested footwear, or all suggested footwear without an inventory check for current availability. After printing the desired information, the user preferably selects to continue program operation and branch point menu/screen display 248, shown in FIG. 32 is presented on display 122. From this menu/screen display, a user may choose to select a shoe for the next person, make changes to current data, return to the fit screen control program, branch to the footwear product catalog, branch to the last overlay viewing program module, or branch to the fit aid recommendations program module.

Figure 23:
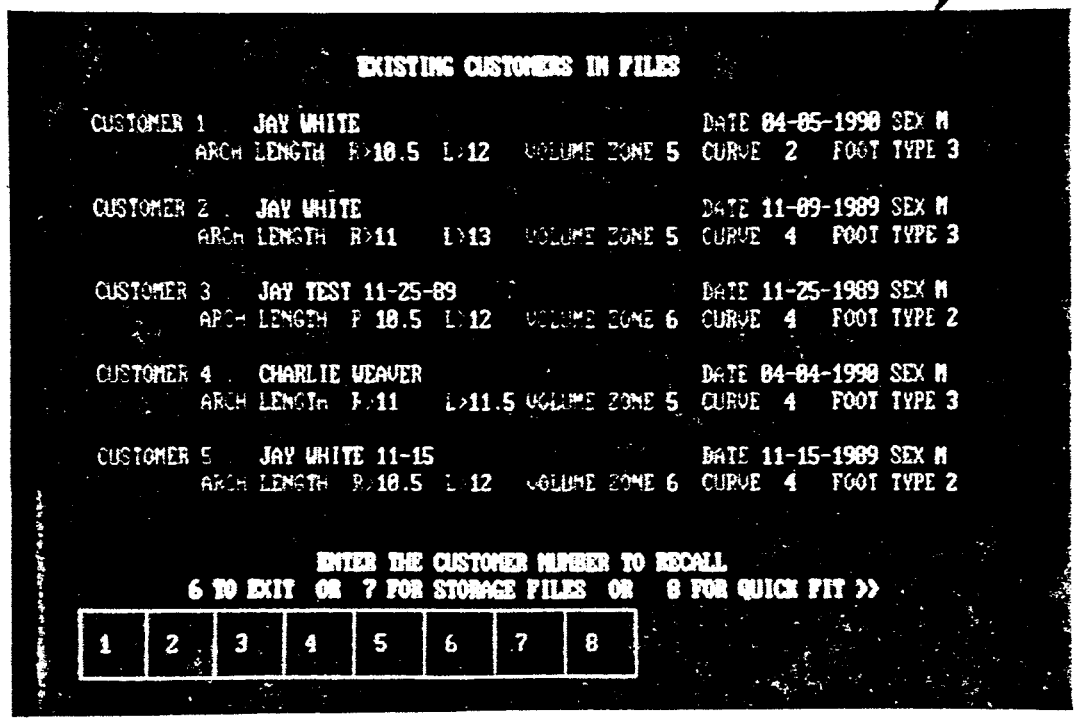
Figure 38:
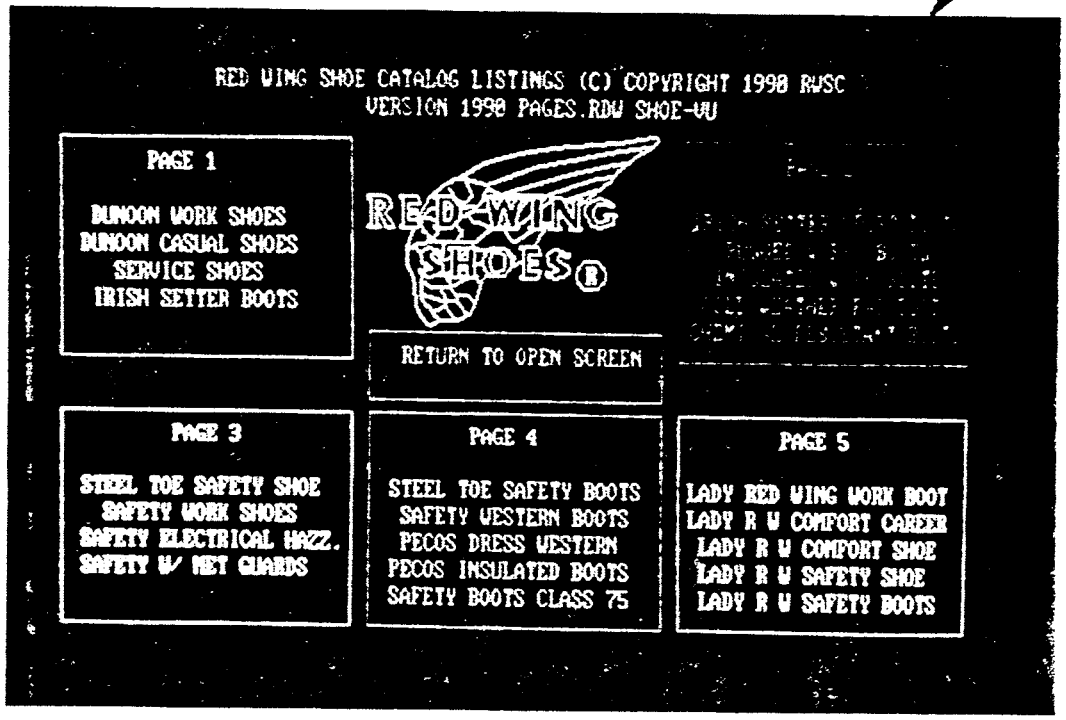
Figure 44:
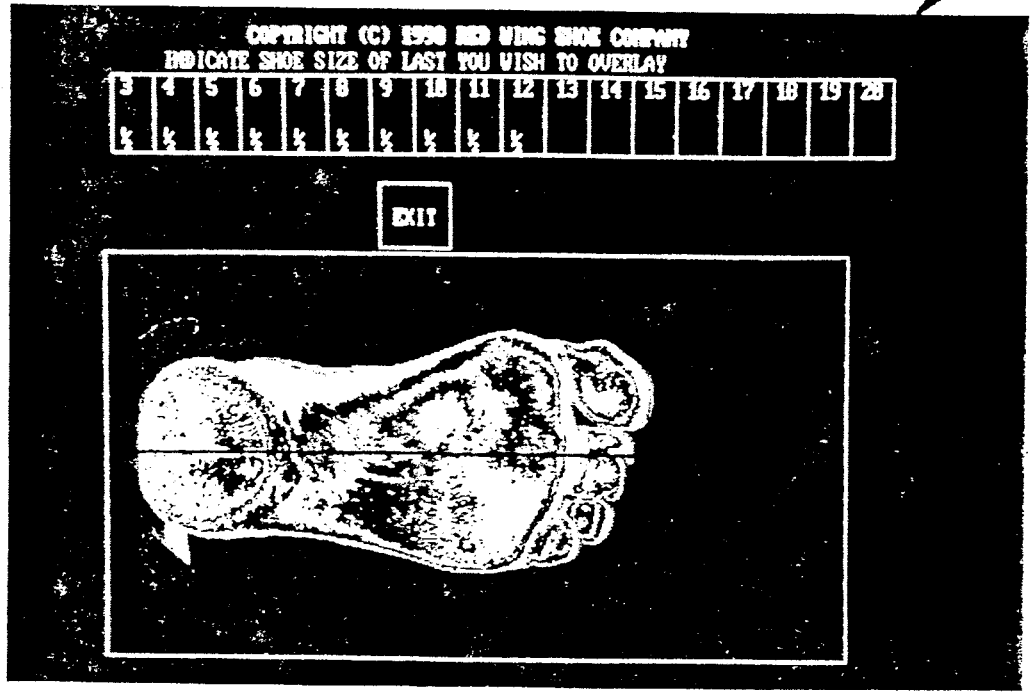
Figure 49:
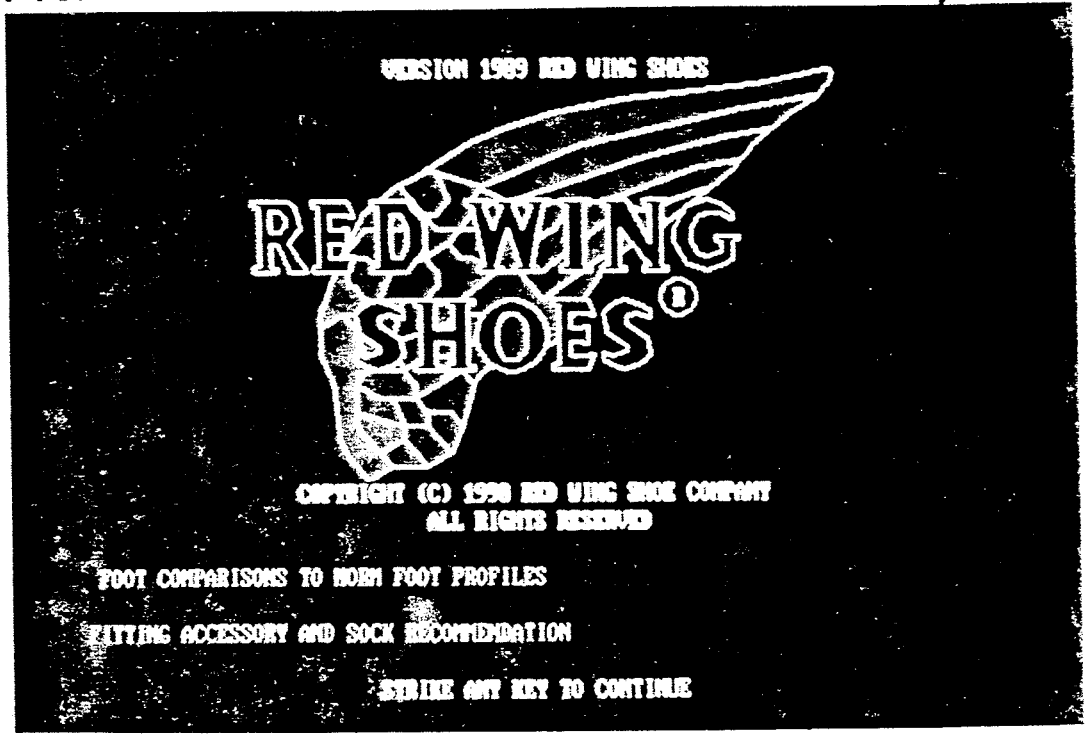

Upon indicating a desire to select a shoe for the next person, central computer 120 branches to menu/screen display 236, shown in FIG. 23, and continues normal operation from that point. Upon indicating to make data changes, central computer 120 branches to menu/screen display 246, shown in FIG. 28, and continues normal operation from that point. Upon indicating a desire to branch to fit/scan control, central computer 120 branches to menu/screen display 200, shown in FIG. 6, and continues normal operation from that point. Alternatively, upon indicating a desire to review the footwear product catalog, menu/screen display 260, as shown in FIG. 38, is presented on display 122 and central computer 120 continues normal operation from that point in the flow diagram shown on FIG. 4C. Alternatively, upon indicating a desire to view last overlay, menu/screen display 272, shown in FIG. 44, is presented on display 122 and normal operation of central computer 120 is continued as shown in the flow diagram shown in FIG. 4C. Alternatively, upon indicating a desire to branch to the fit aid recommendations module, menu/screen display 282, shown in FIG. 49, is presented on display 122 and central computer 120 continues normal operation from that point as shown in program flow diagram FIG. 4A.

Figure 24:
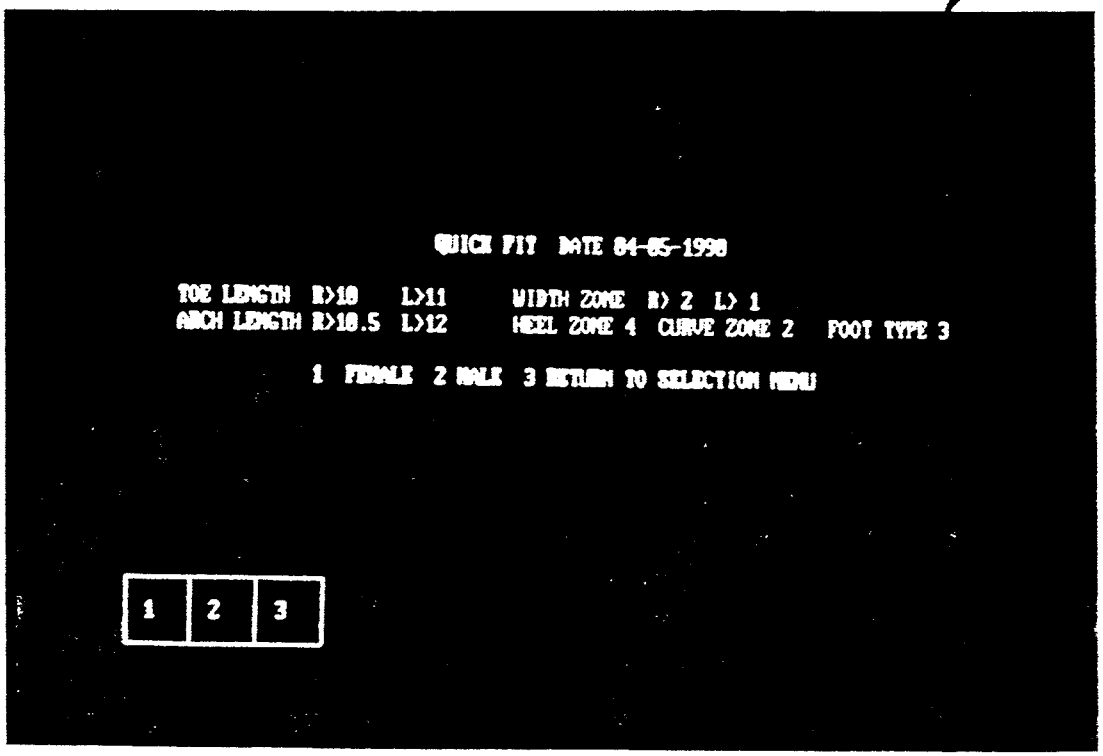

Alternatively, from menu/screen display 210, shown in FIG. 10, a user may choose to enter the quick fit module. The quick fit program module is designed to work with only scan data and without customer information. After choosing to enter the quick fit module, menu/screen display 234, shown in FIG. 22, is presented on display 122. Menu/screen display 234 indicates that central computer 120 is loading footwear information into memory. After accomplishing the loading of such information, menu/screen display 238, shown in FIG. 24, is presented on display 122. After selecting the sex of the quick fit customer, screen display 240 is presented on display 122 and central computer 120 continues on in the program flow as indicated in FIG. 4B and as previously detailed in the discussion of the complete data module.

Figures 33, 34:
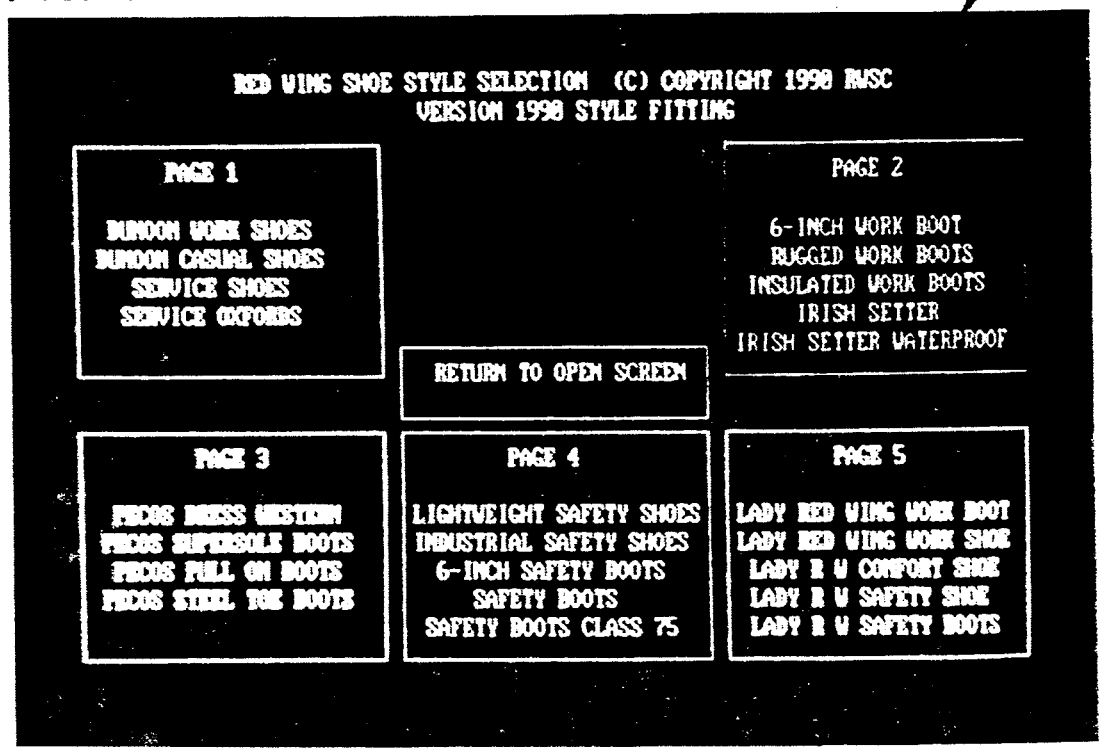

Alternatively, as shown in menu/screen display 210, shown in FIG. 10, the user may select to enter the style fit module. Upon selecting to enter the style fit module, menu/screen display 250, shown in FIG. 33, is presented on display 122. The user is prompted to select a particular style of footwear which they would like to be fitted for. For instance, a user may choose to pick a particular shoe from the selections shown in menu option entitled page 1. After such selection, menu/screen display 252, shown in FIG. 34, is presented on display 122. A user is prompted to select a particular style of footwear for which to be fitted. After selecting a particular style of footwear, menu/screen display 254, shown in FIG. 39, is presented on display 122. Menu/screen display 254 provides particular information about the chosen style of footwear including sizes and widths available according to the Brannock measurement system and particular features of this footwear, including liner, insole, insulation, dressing, construction and sole. A user may choose to return immediately to one of the particular style pages such as page 1, shown in menu/screen display 252, return to the main style menu/screen display 250, or to fit this style.

Figure 37:
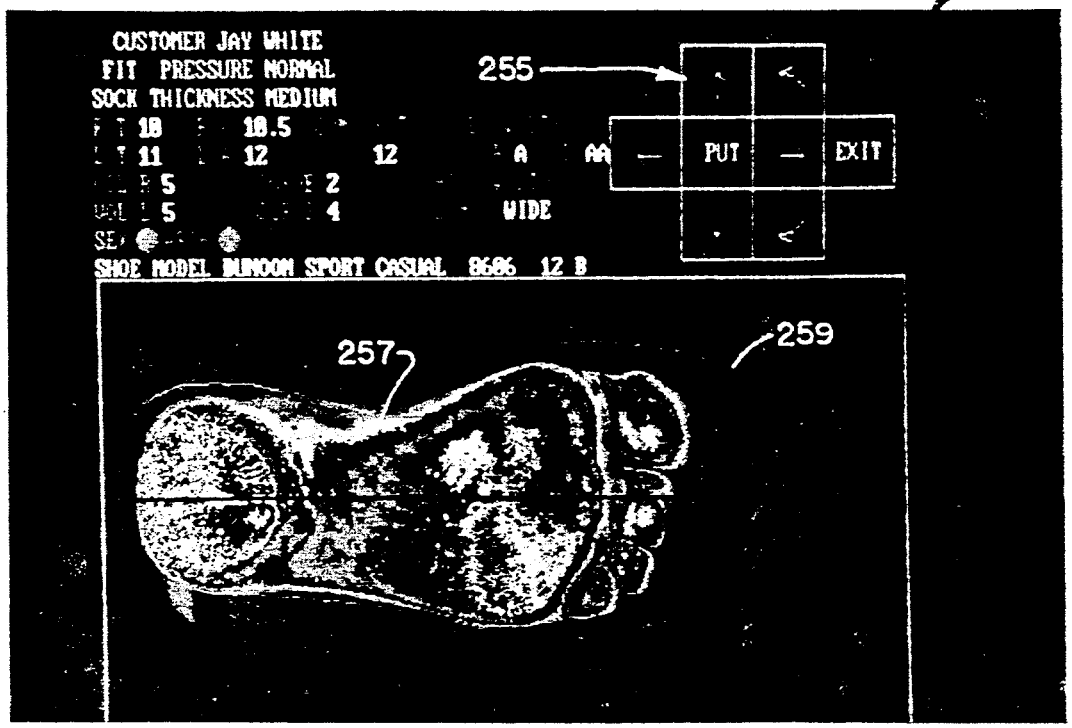

Upon choosing to fit this particular style, menu/screen display 256, shown in FIG. 36, is presented to the user. After entering the particular sex of the customer, last overlay menu/screen display 258, shown in FIG. 37, is presented on display 122. The last overlay menu/screen display 258 shows how the particular chosen style of footwear will fit on the currently selected scanned foot information. The user may move the style last overlay outline 259 with respect to the scanned foot image 257 by selecting movement indicator menu options 255. After viewing the particular style last overlay 259 on the scanned foot, the user selects to return to menu/screen display 250. Subsequently, from menu/screen display 250, the user may choose to return to menu/screen display 200, shown in FIG. 6, or fit another footwear style to the particular foot currently selected.

Figure 41:
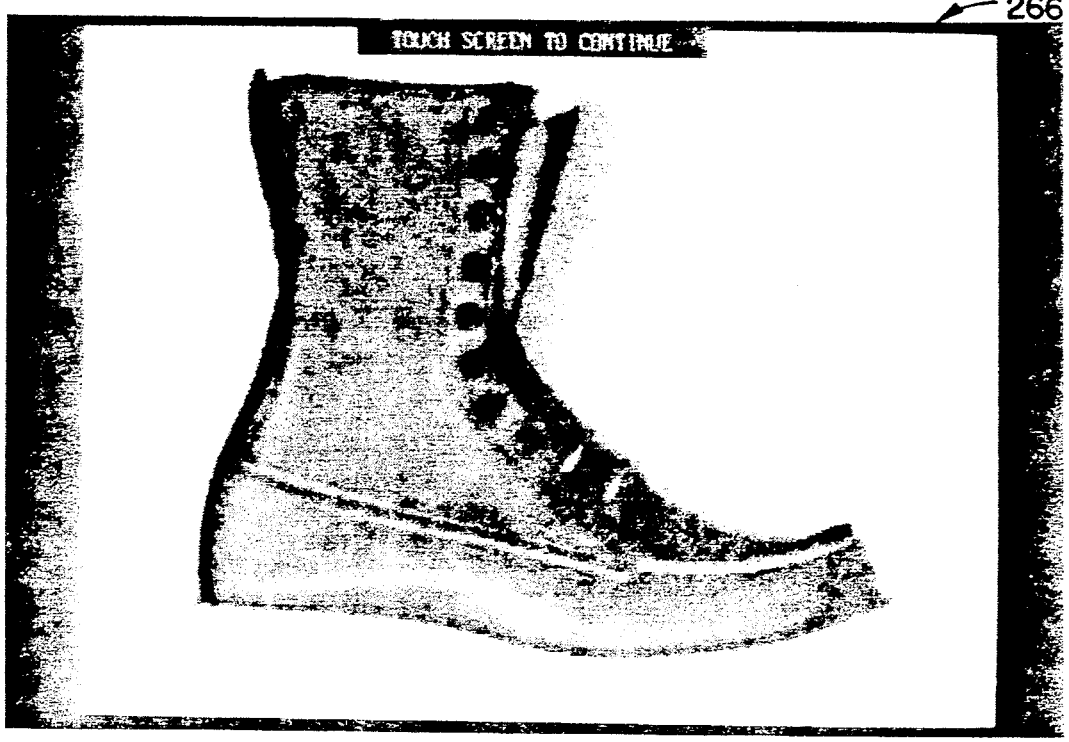
Figure 42:
Figure 43:
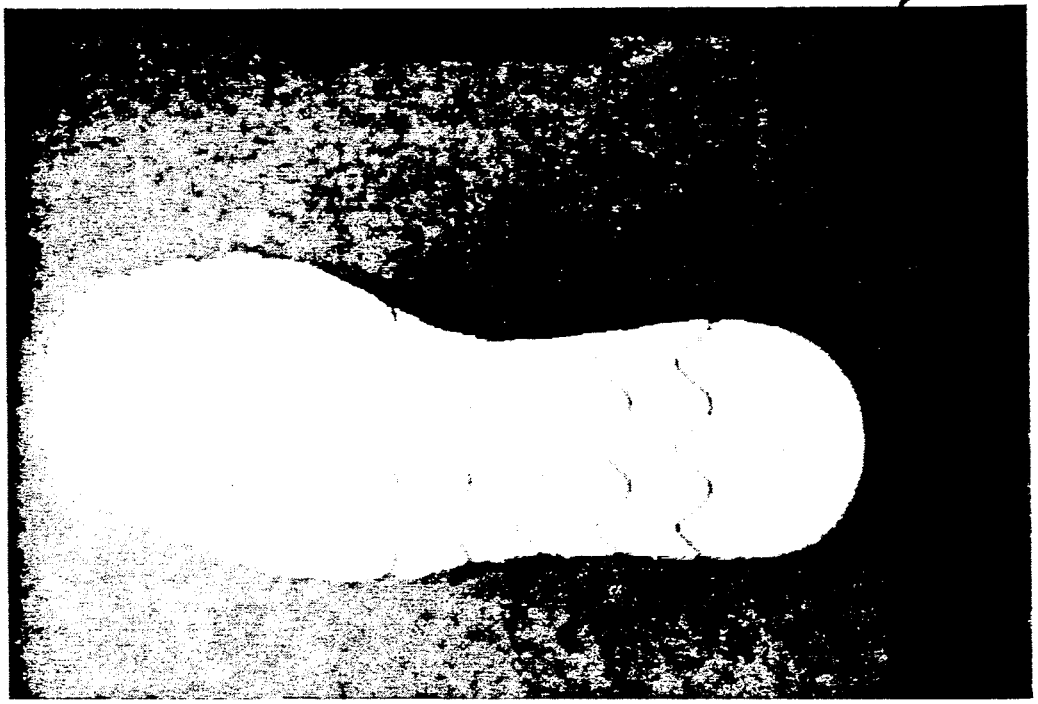

Alternatively, as shown in menu/screen display 210, shown in FIG. 10, the user may select to enter the catalog module. Upon selecting to enter the catalog module, menu/screen display 260, shown in FIG. 38, is presented on display 122. Through menu/screen display 260, a user may browse through the current catalog listings of footwear according to different styles without having previously selected customer information to be used in conjunction with selecting a particular style. The styles available may be presented on display 122 in textual menus as shown in menu/screen display 260. Alternatively, the styles may be shown in graphical depictions of particular styles of shoes available such as hiking boots, running shoes, service shoes, work boots, etc. For example, a user may choose to view shoes from page 3, as shown in menu/screen 262, shown in FIG. 39. The list of particular footwear may be shown in a textual or graphical manner as discussed above. Such that miniature graphical representatives of footwear may be shown in place of the textual listing of the name of the footwear. After viewing the list of particular footwear listed on catalog page 3, a user may choose to view a particular piece of footwear. Upon choosing a particular piece of footwear, menu/screen display 264, shown in FIG. 40, is presented on display 122. Information about the particular footwear selected is presented to the user including sizes and widths available according to the Brannock sizing system and particular features of this particular footwear. A user may choose to return to the same or different pages of the catalog or to the main menu catalog screen 260, shown in FIG. 38. Alternatively, a user may choose to more closely view the particular footwear selected. In the preferred embodiment, menu/screen display 264 includes miniature pictures of the side 263, top 263' and bottom 263" views of the particular footwear selected. A user may choose to more closely view one of these particular views of the footwear selected. Upon choosing to more closely view one of the several views of the selected footwear, one of several larger views of that particular footwear is presented on display 122. For example, screen display 266, 268, and 270, as shown in FIGS. 41, 42 and 43, respectively, are presented on display 122.

Figure 45:
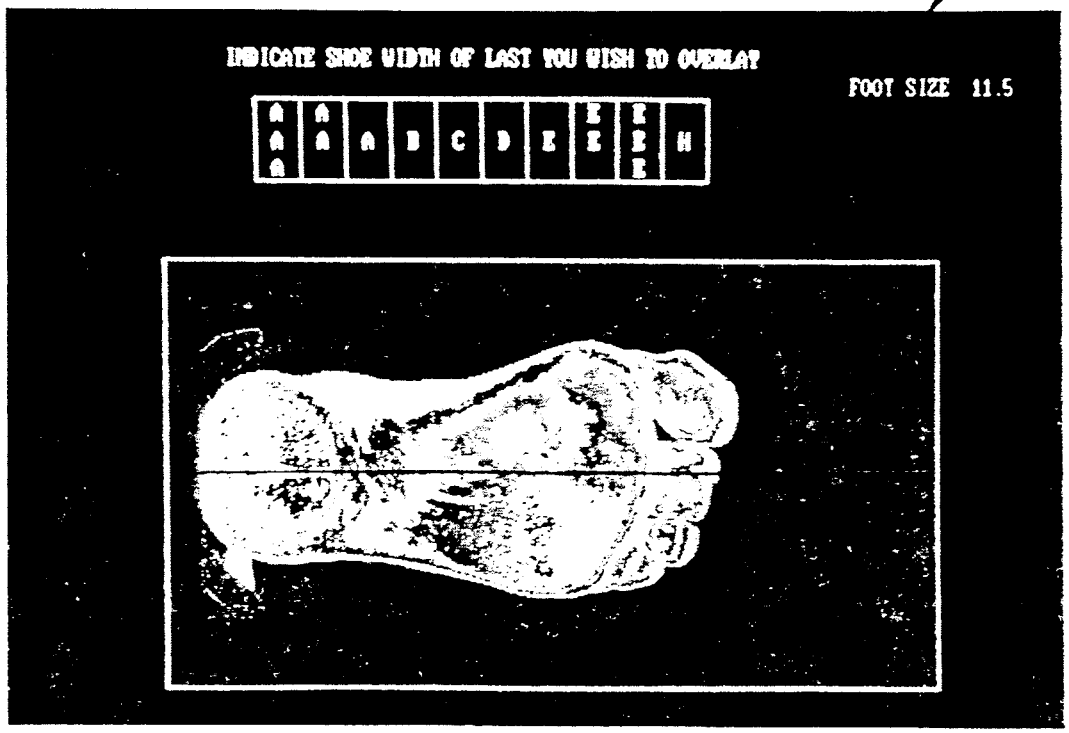
Figure 46:
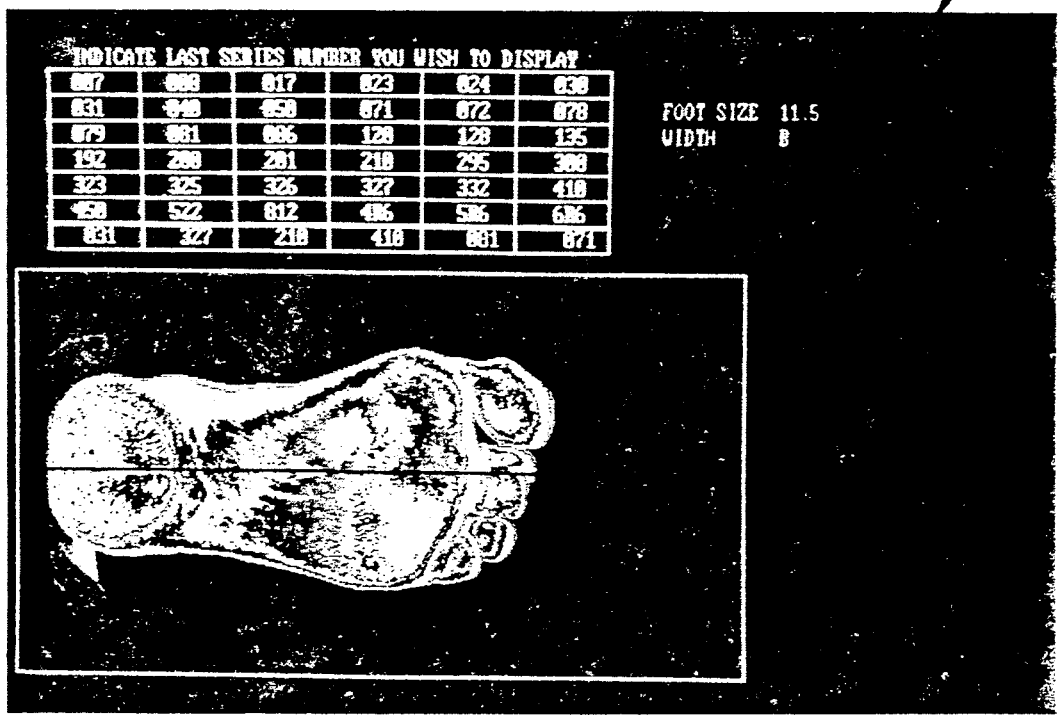
Figure 47:
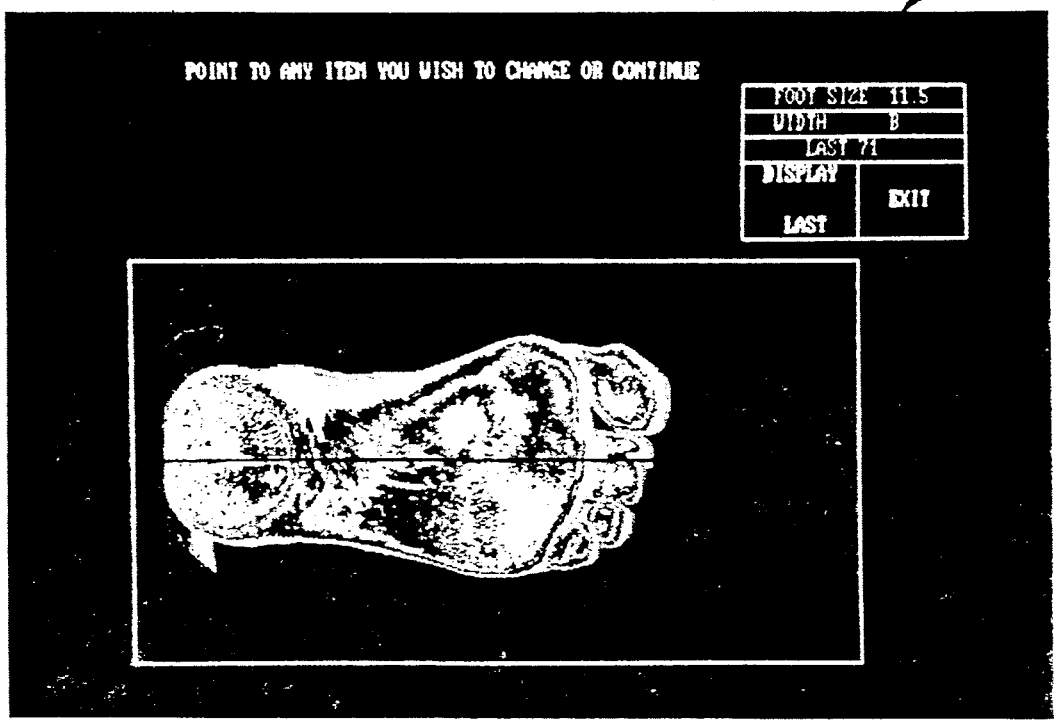
Figure 48:
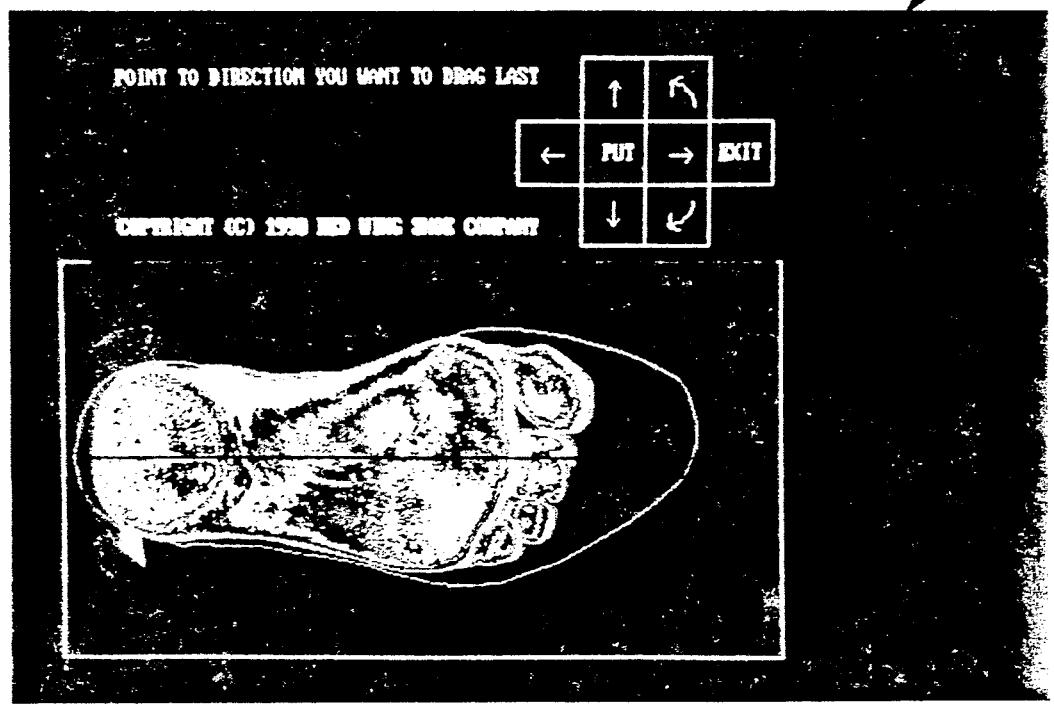

Alternatively, as shown in menu/screen display 200, shown in FIG. 6, the user may select to enter the last overlay module. Upon selecting to enter the last overlay module, menu/screen display 272, shown in FIG. 44, is presented on display 122. After selecting the particular shoe size of the last to be overlaid on the scanned foot, menu/screen display 274, shown in FIG. 45, is presented on display 122. After selecting the width of the last to be overlaid on the scanned foot, menu/screen display 276, shown in FIG. 46, is presented on display 122. After indicating the last series (style of footwear) to be overlaid on the scanned foot, menu/screen display 278, shown in FIG. 47, is presented on display 122. The user is prompted to change any of the last overlay parameters, return to the main menu/screen display 200 through branch 302, or to overlay the last outline on the scanned foot image. Upon choosing to display the last overlay on the scanned foot image, menu/screen display 280, shown in FIG. 48, is presented on display 122. The outline of the last may be moved with respect to the scanned foot image through the use of overlay movement menu options so that a user can see how a particular style and size of footwear will fit on the particular scanned foot. After viewing how the particular selected last fits the scanned foot image and choosing to exit menu/screen display 280, menu/screen display 272, shown in FIG. 44, is presented on display 122 and central computer 120 continues normal operation from that point as shown in the program flow diagram FIG. 4C.

Figure 65:
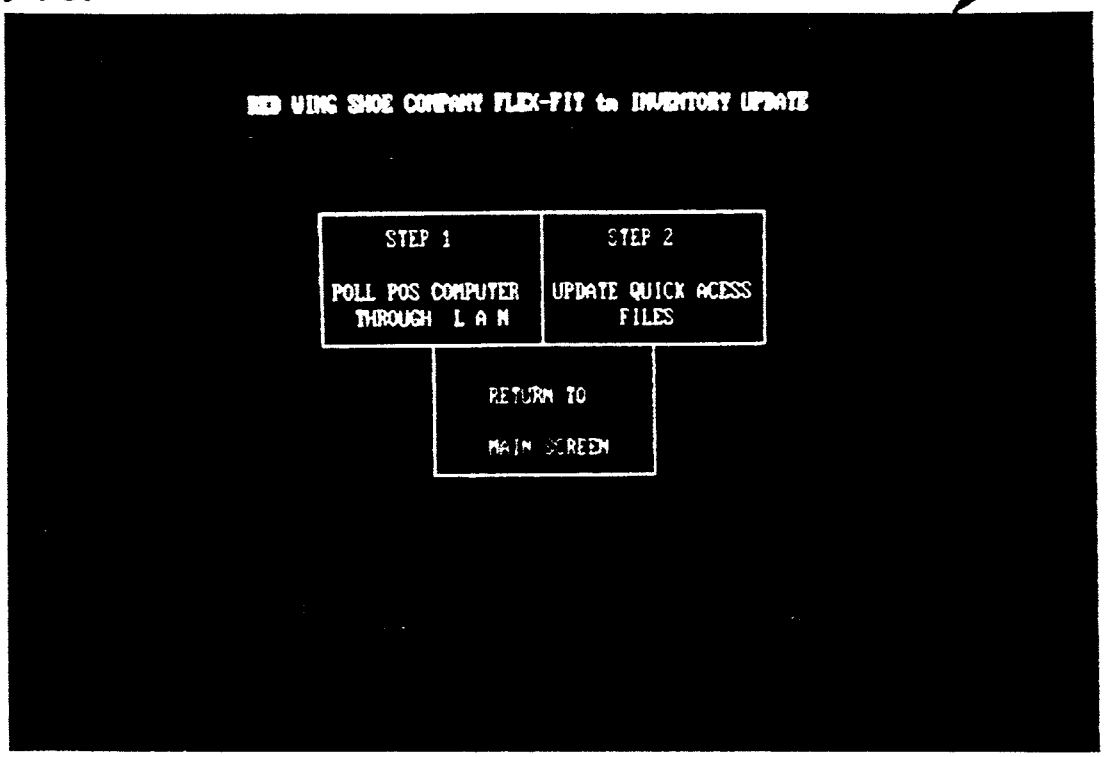
Figure 66:
Figure 67:
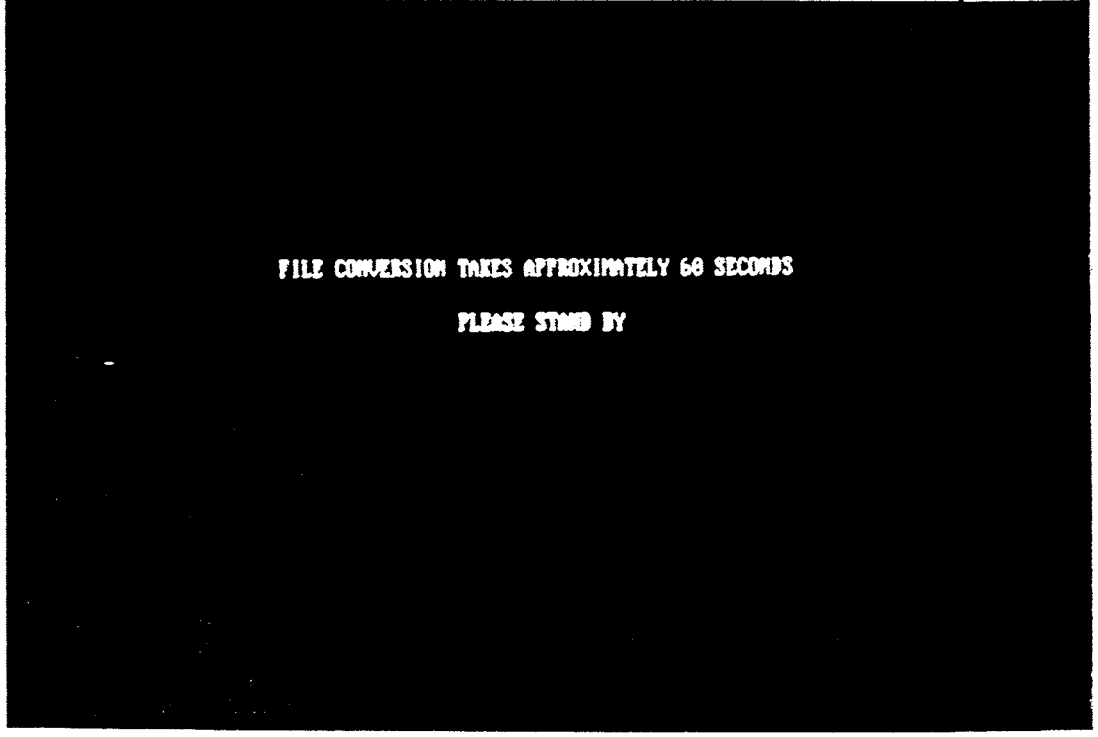

Alternatively, a hidden option on menu/screen display 200, shown in FIG. 6, is available. Upon activation of the hidden menu option in menu/screen display 200, central computer 120 operates interactively with remotely stored inventory data 124 as shown in FIG. 4C. Upon selection of the hidden option, menu/screen display 330, shown in FIG. 65, is presented on display 122. The user is prompted to update inventory information. Upon choosing the first updating step, including polling a remotely located computer including inventory data 124, menu/screen display 332, shown in FIG. 66, is presented on display 122 while central computer 120 receives information from remotely located inventory data 124. After receiving the inventory data 124, menu/screen display 330 is presented on display 122. Upon selecting the second updating step of updating quick access files, menu/screen display 334, shown in FIG. 67, is presented on display 122. After updating the quick access files, menu/screen display 330 is presented on display 122. Preferably, the user chooses to return to main open menu/screen display 200, shown in FIG. 6, and central computer 120 continues on in the program flow as indicated in FIG. 4A.

Figure 50:
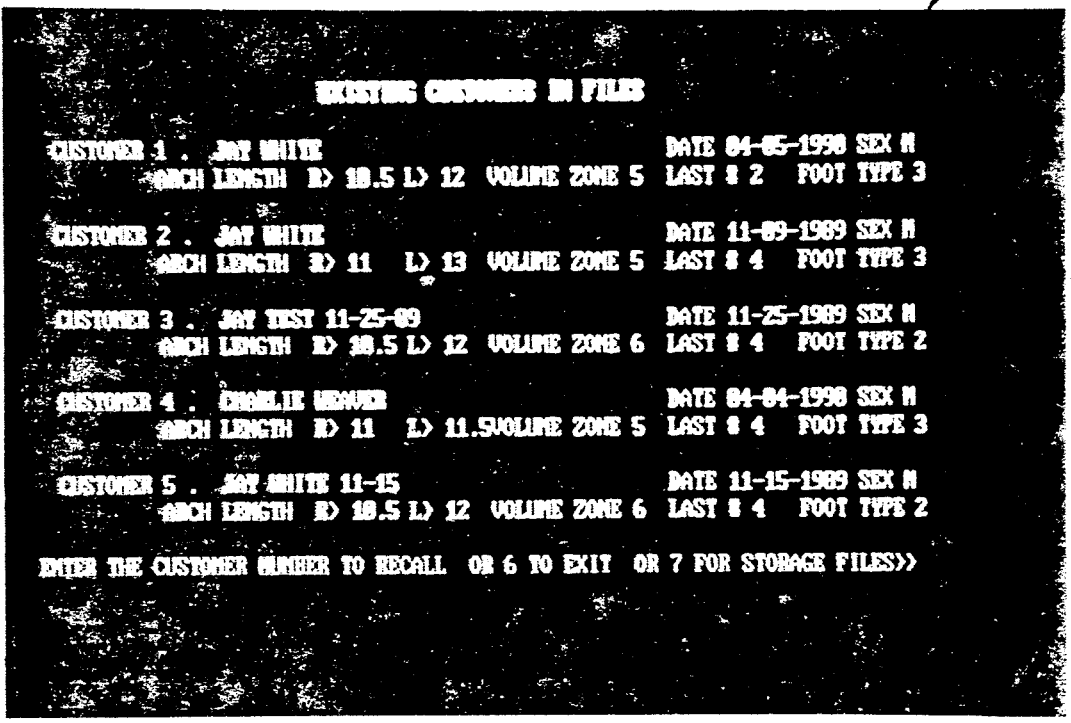
Figure 51:
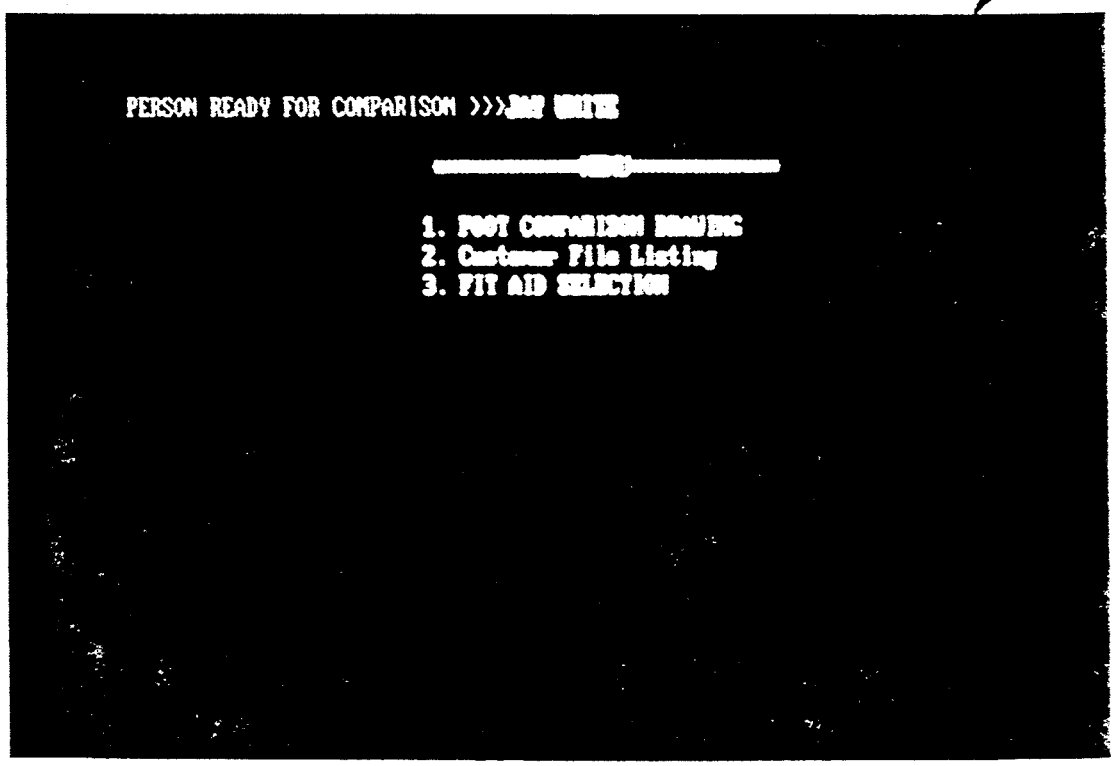

Alternatively, from open menu/screen display 200, shown in FIG. 6, or through branch point 310, the fit aids module may be entered. Upon entering the fit aids module, menu/screen display 282, shown in FIG. 49, is presented on display 122. If a customer file has not been previously selected, menu/screen display 284, shown in FIG. 50, is presented on display 122 so that a user may select a particular customer for which to suggest fit aids. The user may choose to enter a current customer number, return to open main menu/screen 200, or retrieve customer information from storage device 130.

Figure 52:
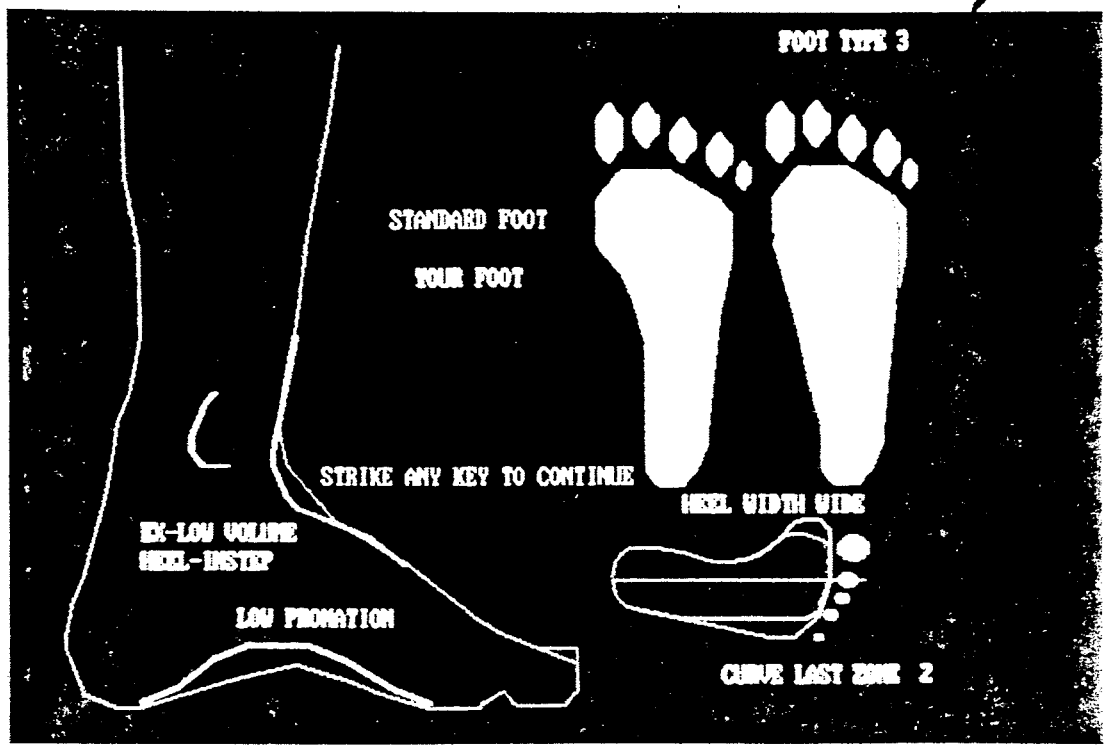

Alternatively, if a particular customer file has already been selected prior to entering menu/screen display 282, then menu/screen display 284 is not shown on display 122. In either situation, after a particular customer file has been selected, branch point menu/screen display 286, shown in FIG. 52, is presented on display 122. From branch point menu/display screen 286, the user may choose to display a foot comparison of the selected customer foot image compared to a standard foot. Upon selecting foot comparison display, menu/screen display 288, shown in FIG. 52, is presented on display 122. Information concerning the variation of the particular customer foot from a standard foot is given. For instance, in the example foot shown in menu/screen display 288, the selected foot has a wide heel width, low pronation and extra low volume. After viewing the foot comparison, menu/screen display 286 is returned to for continued program operation.

Alternatively, from branch point menu/screen display 286, a user may choose to go to menu/screen display 284 and select a different customer file. Alternatively, from branch point menu/screen display 286, the user may choose to select fit aids. Upon choosing to select fit aids, menu/screen display 290, shown in FIG. 53, is presented on display 122. Menu/screen display 290 provides fit aid recommendations for the particular selected customer foot including items such as a heel cup, heel cushion, wedge, arch support, forefoot cushion, volume adjust shim, and the like. In addition, the prices for each of the fit aid products are provided for customer feedback. Further, suggested socks and prices are presented so that a user may choose the best socks available in the retail store based on previously entered customer preferences for the particular foot. After displaying all of the recommended fit aids for the particular customer, a user may generate a hard copy on printer 128 of the suggested fit aids, draw a picture of the particular suggested fit aids or branch to an alternative branch point menu. Upon choosing to display suggested fit aids for the particular customer, a menu/screen display 292, like the one shown in FIG. 54, is presented on display 122. In menu/screen display 292, only the suggested fit aids for the particular selected customer foot image file are shown. For instance, in the example shown, the suggested fit aids include a Red Wing insole, heel cup, heel cushion, metatarsal support and volume adjust shim. After viewing the suggested fit aids for the selected customer fit image file, menu/screen display 290 is redisplayed.

Figure 55:
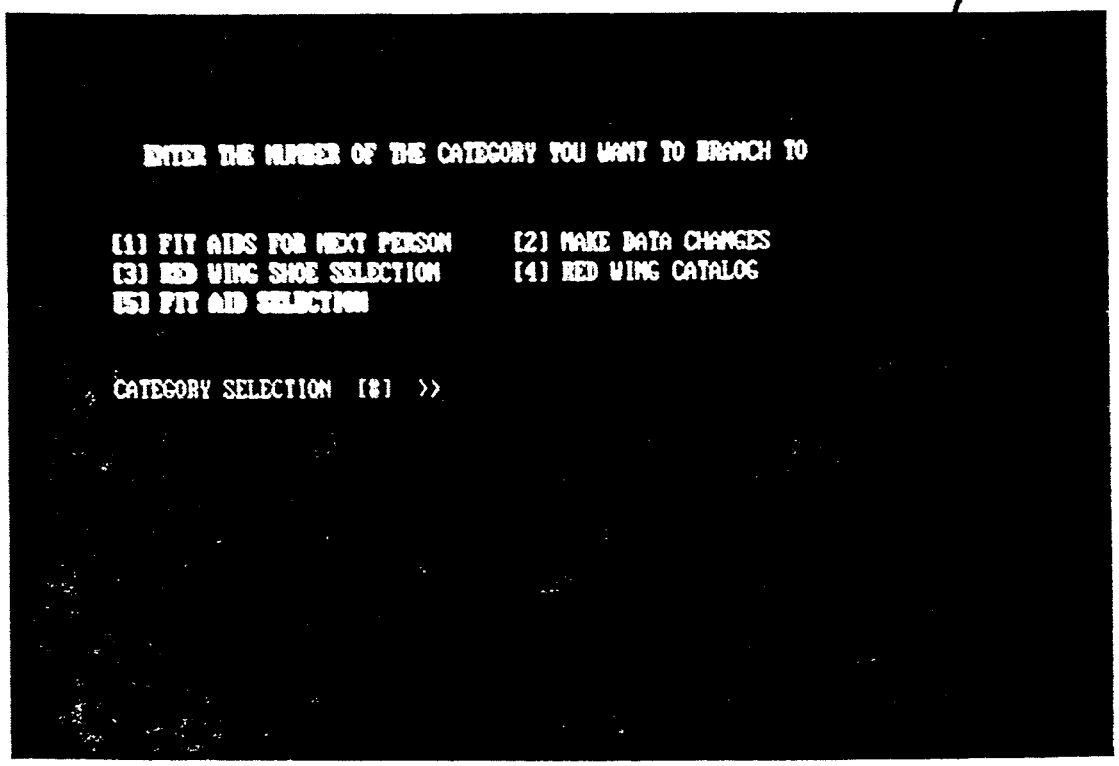
Figure 56:
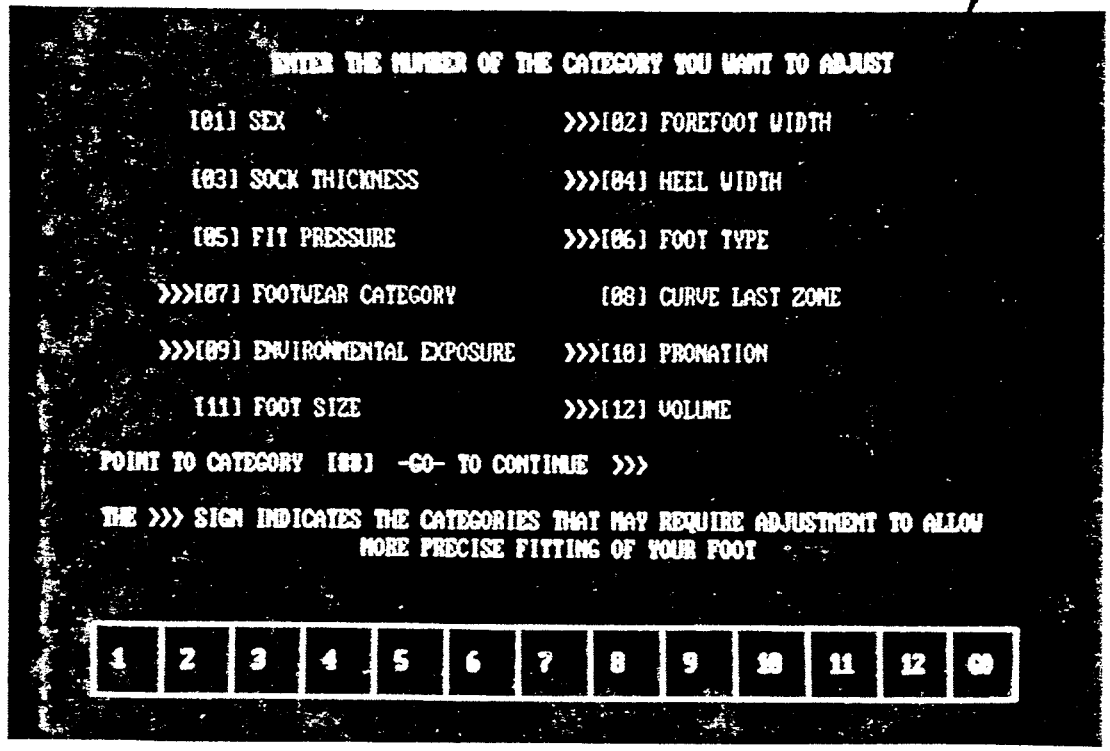

Upon choosing to go to a return menu, branch point menu/screen display 294, shown in FIG. 55, is presented on display 122. From the branch point menu/screen display 294, the user may choose to return to the beginning of the fit aid module through branch point 310 and choose fit aids for the next customer. Alternatively, a user may choose to adjust the fitting specifications through the use of menu/screen display 295, shown in FIG. 56, which functions in a similar manner to the adjust fitting specification operation described for menu/screen displays 246 and 247, shown in FIGS. 30 and 31, respectively. Alternatively, a user may choose to select a particular style of footwear by branching to the style fit module through branch point 312. Alternatively, a user may choose to view the footwear catalog by branching through branch point 306 to the catalog module. Alternatively, a user may choose to return to the fit aid recommendations menu/screen display 290 and continue program operation through central computer 120.

Figure 59:
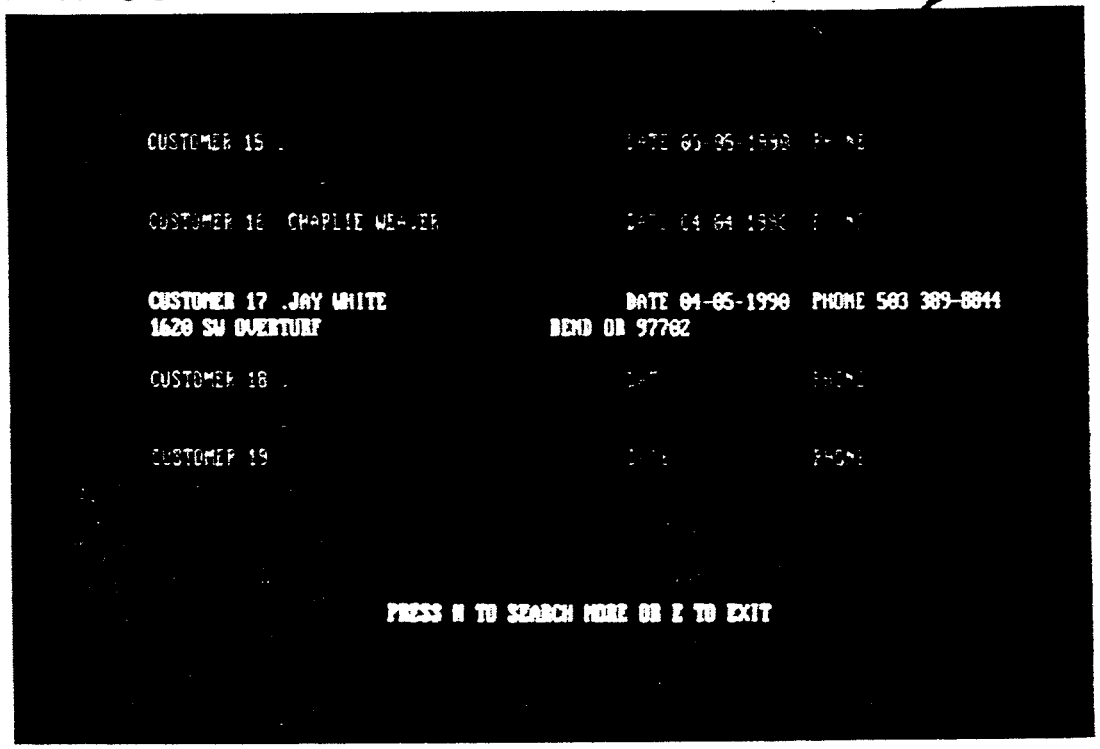

Alternatively, from open menu/screen display 200, shown in FIG. 6, a user may choose to enter the file locator module. Upon entering the file locator module, menu/screen display 296, shown in FIG. 57, is presented on display 122. From menu/screen display 296, a user may choose to search storage device 130 by one of several search methods including searching by customer number, alphabetical search, the date that the customer file was first entered, and a simple incremental search. In addition, from menu/screen display 296, the user may generate a label and print a hard copy on printer 128 and return to open menu/screen display 200. After choosing the particular search method, for instance by an alphabetical search, menu/screen display 298, shown in FIG. 58, is presented on display 122. The user is prompted to input a string of characters which is to be searched for in storage device 130. After entering the string of characters to be searched for, a menu/screen display 300, such as the one shown in FIG. 59, is presented on display 122. Menu/screen display 300 preferably displays the first customer file record found which matches the search string as well as the preceding two customer file records and the following two customer file records. In addition, a user may choose to find the next customer file record containing the search character string or exit to menu/screen display 296.

Figure 5:
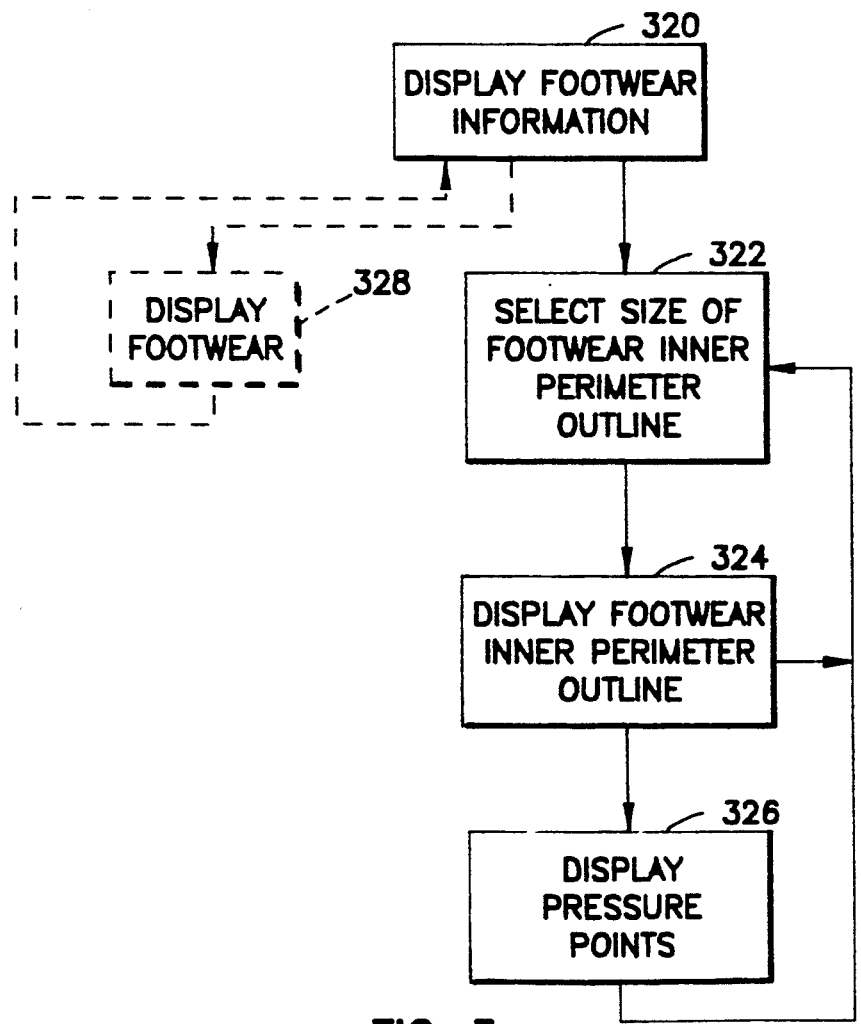
FIG. 5 shows a flowchart diagramming an alternative example of operating a preferred embodiment electro-optical scanner unit from a user's point of view.
Figure 60:
Figure 64:
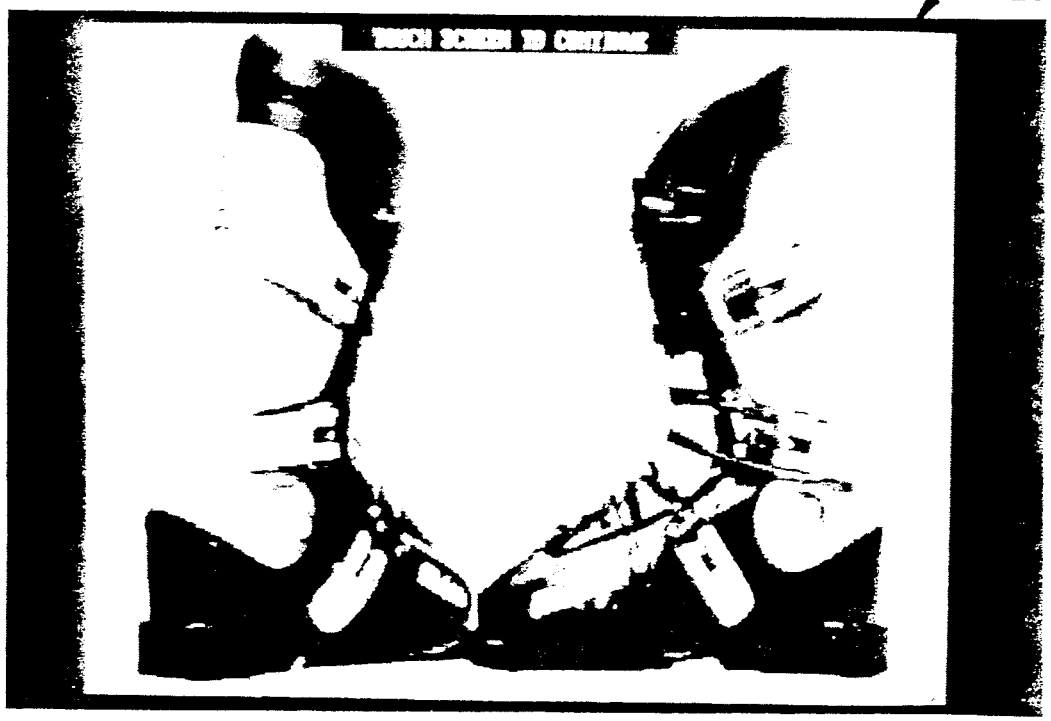

In alternative embodiment, as shown in FIG. 5, footwear information can be displayed in a plurality of different ways. In this example, ski boot footwear is being displayed. However, it will be appreciated by those skilled in the art that the principle shown herein may be applied to all forms of footwear. Ski boot footwear information is displayed in menu/screen display 320 as shown in FIG. 60. Ski boot information includes various parameters which are utilized by the ski boot industry including flex index with volume pronation and several features of the particular ski boot including buckle type fit material, liner cover, liner features, foot bed type, foot bed adjustability, shell type, shell materials, and shell features. From menu/screen display 320, a user may choose to view the particular ski boot by selecting the computer graphic image of the ski boot. After selecting the computer graphic image of the ski boot, menu/screen display 328, as shown in FIG. 64, is presented on display 122. After viewing the ski boot image, the user returns to menu/screen display 320.

Figure 61:
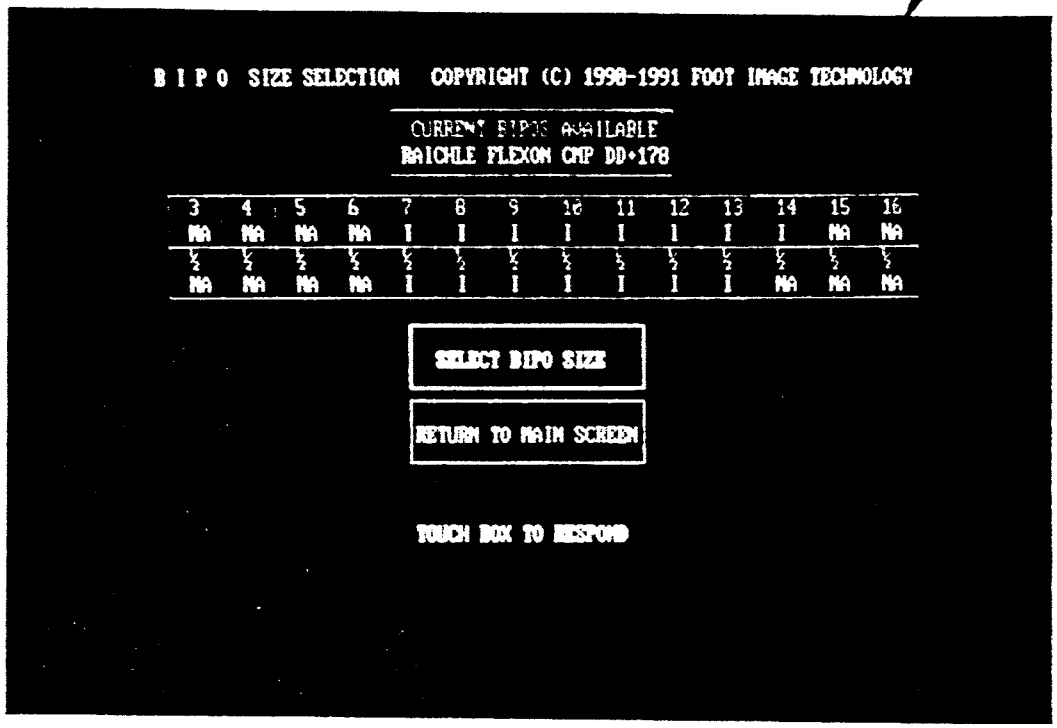
Figure 62:
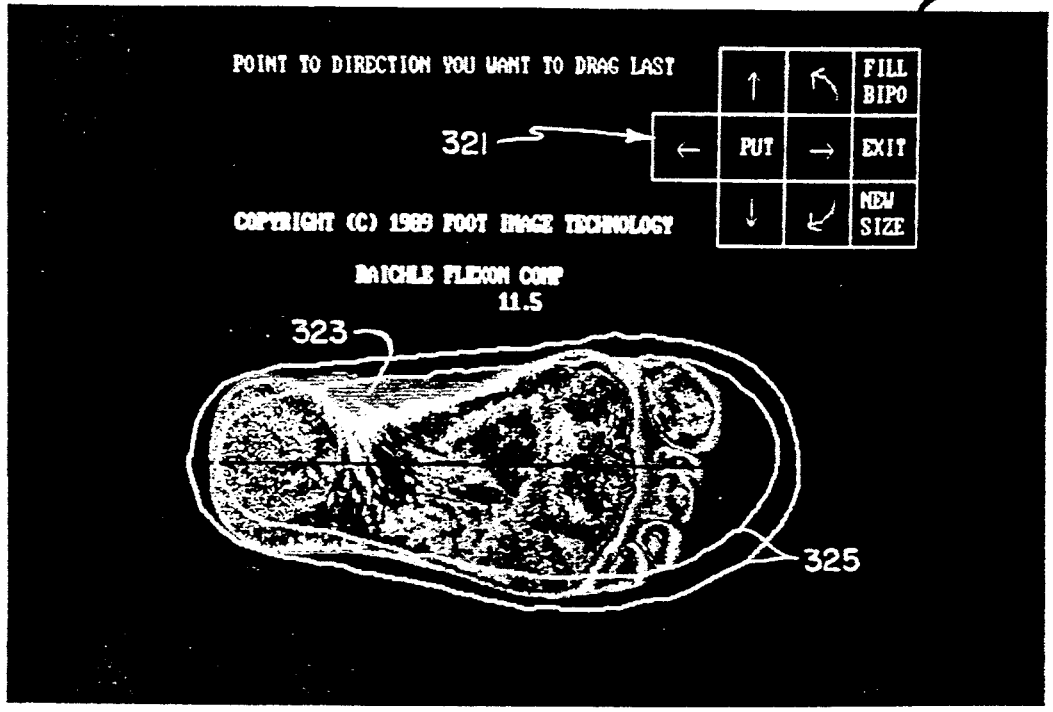
Figure 63:
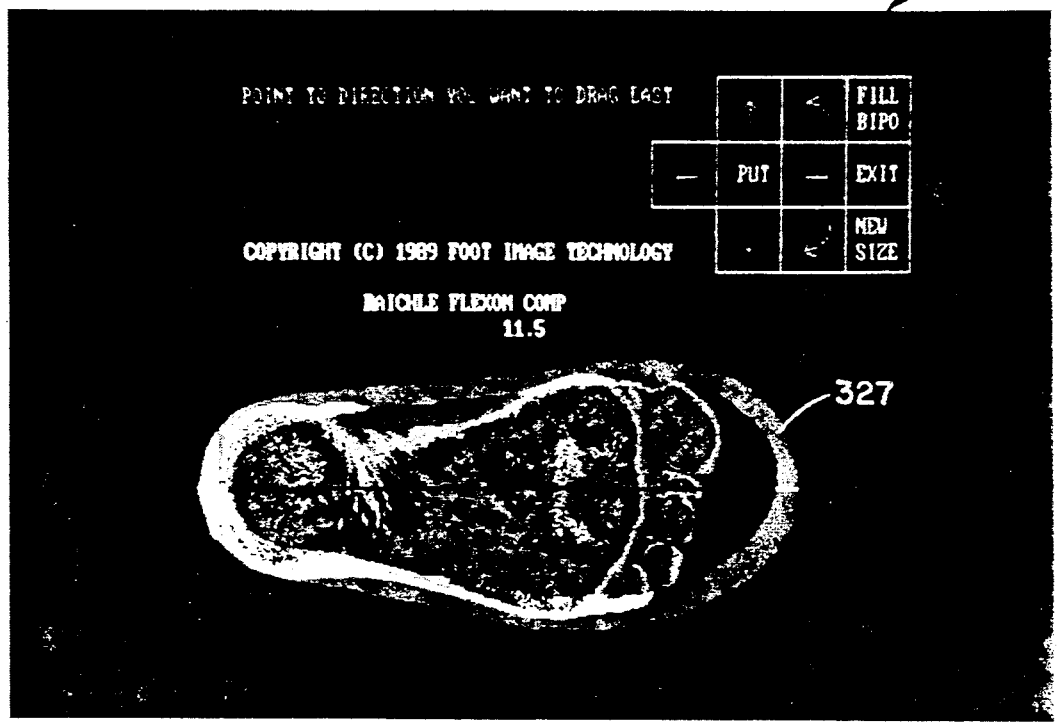

In addition, the user may choose to view an alternative last overlay tailored for footwear having sidewall liners, or liners and an outer shell. After choosing to view this alternative last overlay, menu/screen display 322, shown in FIG. 61, is presented on display 122. The user may select a particular boot internal perimeter outline (BIPO) to overlay the scanned foot image currently selected by selecting a particular BIPO size. After selecting the particular BIPO size to overlay on the image 323 of the scanned foot currently selected, menu/screen display 324, shown in FIG. 62, is presented on display 122. As shown in menu/screen display 324, a double-lined boot image 325 (also referred to as a liner region image) is overlaid on a scanned foot image. By manipulating menu options 321, the double-lined boot image outline 325 may be moved with respect to the foot image. After placing the boot image 325 precisely, a user may choose to show the particular pressure points between the boot and scanned foot image. Upon choosing to view the pressure points, menu/screen 326, as shown in FIG. 63, is presented on display 122. Menu/screen display 326 displays a filled boot outline image 327 between the two-lined image 325 shown in menu/screen display 324. In addition, portions of the foot image 323 which are between the inner (the line generally nearer the foot image) and outer lines (the line generally further from the foot image) of the filled boot image 257 are highlighted so that a user may discern the amount of pressure a foot would encounter from the inner lining pressing against the foot. This allows the user to adjust the size of the boot desired to properly fit the scanned foot with an optimally chosen size of boot and liner in accordance with the pressure preferences for the owner of the particular foot which has been scanned. From menu/screen display 326, a user may choose to adjust the size of the boot image by returning to menu/screen display 322 or exit the display footwear information module.

Although the present invention has been described and illustrated with a certain degree of particularity, it is understood that the present disclosure of embodiments has been made by way of example only and that numerous changes in arrangement and combination of parts as well as steps may be resorted to by those skilled in the art without departing from the spirit and scope of the present invention as claimed. In particular, it will be appreciated by those skilled in the art that a plurality of foot measurement techniques are available for use in such a system, including the Brannock measurement system and the TWAC ™ measurement system. In addition, the hardware and software components used for the present invention may be modified in view of future technological improvements including, but not limited to, faster computing devices, higher resolution displays and improved electro-optical scanners or other devices for capturing the three-dimensional image of a foot.

What is claimed is:

1. A system for mapping surfaces of a foot, the system comprising:
   a) a reference surface permitting viewing of the foot from below a bottom surface of the foot when the foot is positioned above the reference surface;
   b) a light source positioned to project light on the bottom surface of the foot;
   c) optical measuring means for measuring light reflected off of the foot to determine light intensity levels and color levels of the foot;
   d) processing means for converting the optically determined light intensity levels of the light reflected off the foot into distance values representing distances of the foot from the reference surface; and the processing means further converting the optically determined color levels of the light reflected off of the foot into pressure values representing pressures exerted by the foot on the reference surface; and
   e) display means for displaying the distance values so that portions of the foot surfaces which are closer to the reference surface are differentiated from other portions of the foot surfaces which are relatively distant from the reference surface, the display means further displaying the pressure values so that portions of the foot surfaces which are exerting greater pressure against the reference surface are differentiated from other portions of the foot surfaces which are exerting less pressure against the reference surface.

2. The system of claim 1, wherein the display means further displays the distance values so that portions of the foot surfaces which are closer to the reference surface appear in closer three dimensional visual relief in comparison with other portions of the foot surfaces which are relatively distant from the reference surface.

3. The system of claim 2, wherein the display means further displays the pressure values so that portions of the foot surfaces which are exerting greater pressure against the reference surface appear in closer three dimensional visual relief in comparison with other portions of the foot surfaces which are exerting less pressure against the reference surface.

4. The system of claim 1, wherein the display means further displays the distance values so that portions of the foot surfaces which are closer to the reference surface than other portions of the foot are displayed with colors of greater wavelength or gray scale values of greater intensity than the portions of the foot which are relatively distant.

5. The system of claim 4, wherein the display means further displays the pressure values so that portions of the foot surfaces exerting greater pressure against the reference surface than other portions of the foot are displayed with colors of greater wavelength or gray scale values of greater intensity than the portions of the foot exerting less pressure.

6. A method of measuring the displaying surfaces of a foot, the method comprising the steps of:
 a) placing a bottom surface of a foot adjacent a top of a reference surface;
 b) projecting light against the bottom surface of the foot;
 c) optically measuring light reflected off of the foot to determine light intensity levels and color levels of the foot; and
 d) assigning distance values to the optically determined light intensity levels of the foot;
 e) assigning pressure values to the optically determined color levels of the foot;
 f) displaying the distance values to show relative distances from the reference surface of different portions of the foot surfaces; and
 g) displaying the pressure values to show relative pressures exerted against the reference surface by different portions of the foot surfaces.

* * * * *